United States Patent
Okada et al.

(10) Patent No.: US 10,577,323 B2
(45) Date of Patent: Mar. 3, 2020

(54) COMPOUND, RESIN, MATERIAL FOR FORMING UNDERLAYER FILM FOR LITHOGRAPHY, COMPOSITION FOR FORMING UNDERLAYER FILM FOR LITHOGRAPHY, UNDERLAYER FILM FOR LITHOGRAPHY, PATTERN FORMING METHOD, AND METHOD FOR PURIFYING COMPOUND OR RESIN

(71) Applicant: Mitsubishi Gas Chemical Company, Inc., Tokyo (JP)

(72) Inventors: Kana Okada, Kanagawa (JP); Junya Horiuchi, Kanagawa (JP); Takashi Makinoshima, Kanagawa (JP); Masatoshi Echigo, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 15/557,747

(22) PCT Filed: Mar. 9, 2016

(86) PCT No.: PCT/JP2016/057438
§ 371 (c)(1),
(2) Date: Sep. 12, 2017

(87) PCT Pub. No.: WO2016/147989
PCT Pub. Date: Sep. 22, 2016

(65) Prior Publication Data
US 2018/0065930 A1 Mar. 8, 2018

(30) Foreign Application Priority Data
Mar. 13, 2015 (JP) .................... 2015-050731

(51) Int. Cl.
| G03F 7/11 | (2006.01) |
| G03F 7/26 | (2006.01) |
| C07D 209/86 | (2006.01) |
| C07D 405/04 | (2006.01) |
| C08G 61/12 | (2006.01) |

(52) U.S. Cl.
CPC ......... C07D 209/86 (2013.01); C07D 405/04 (2013.01); C08G 61/12 (2013.01); G03F 7/11 (2013.01); G03F 7/26 (2013.01)

(58) Field of Classification Search
CPC ....... C07D 405/04; C07D 209/86; G03F 7/11; C08G 61/12
See application file for complete search history.

(56) References Cited

U.S. PATENT DOCUMENTS

| 4,154,463 | A * | 5/1979 | Burri ...................... B41M 5/136 106/31.2 |
| 4,598,036 | A | 7/1986 | Iwasaki et al. |
| 5,073,622 | A * | 12/1991 | Wojtech .................. C08G 8/10 528/129 |
| 5,189,188 | A * | 2/1993 | Eckstein ................. C09B 11/04 544/102 |
| 9,316,913 | B2 * | 4/2016 | Echigo .................. C07D 311/96 |
| 9,920,024 | B2 * | 3/2018 | Echigo .................. C07D 311/92 |
| 2005/0255712 | A1 | 11/2005 | Kato et al. |
| 2010/0316950 | A1 * | 12/2010 | Oguro .................... C08G 10/02 430/270.1 |
| 2012/0077345 | A1 * | 3/2012 | Saito ...................... C08G 12/26 438/703 |
| 2012/0171611 | A1 | 7/2012 | Ideno et al. |
| 2014/0248561 | A1 * | 9/2014 | Echigo ................. C07D 311/96 430/281.1 |
| 2015/0090691 | A1 * | 4/2015 | Echigo ................. C07D 311/96 216/49 |
| 2015/0301452 | A1 * | 10/2015 | Park .......................... C23F 1/16 216/13 |
| 2016/0222248 | A1 * | 8/2016 | Endo ........................ B05D 1/38 |
| 2017/0001972 | A1 * | 1/2017 | Echigo ................. C07D 311/92 |
| 2018/0246409 | A1 * | 8/2018 | Toida ........................ G03F 7/38 |
| 2019/0041750 | A1 * | 2/2019 | Toida ................... C07D 311/78 |

FOREIGN PATENT DOCUMENTS

| DE | 2112416 A1 | 10/1971 |
| DE | 3433026 A | 3/1985 |

(Continued)

OTHER PUBLICATIONS

Gupta et al., "The synthesis and photo-physical properties of extended styryl fluorescent derivatives of n ethyl carbazole", dyes and pigments vol. 88 378-384 (2011).*

(Continued)

Primary Examiner — Martin J Angebranndt
(74) Attorney, Agent, or Firm — Fitch, Even, Tabin & Flannery LLP

(57) ABSTRACT

A compound represented by the following formula (1).

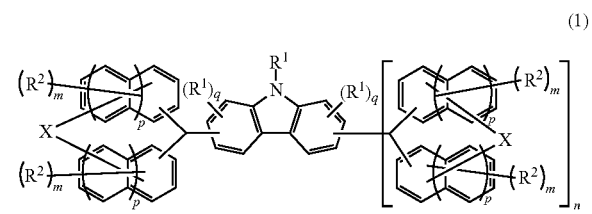

(1)

(in formula (1), each X independently represents an oxygen atom, a sulfur atom, or non-crosslinking, each $R^1$ is independently selected from the group consisting of a hydrogen atom, a halogen group, a nitro group, an amino group, a hydroxyl group, an alkyl group having 1 to 30 carbon atoms, an alkenyl group having 2 to 30 carbon atoms, an aryl group having 6 to 40 carbon atoms and combinations thereof, in which the alkyl group, the alkenyl group and the aryl group may have an ether bond, a ketone bond or an ester bond, each $R^2$ independently represents a linear, branched or cyclic alkyl group having 1 to 30 carbon atoms, an aryl group having 6 to 40 carbon atoms, an alkenyl group having 2 to 30 carbon atoms, a thiol group or a hydroxyl group, in which at least one $R^2$ represents a group having a hydroxyl group or a thiol group, each m is independently an integer of 1 to 7, each p is independently 0 or 1, each q is independently an integer of 0 to 4, and n is 0 or 1.)

12 Claims, No Drawings

(56) References Cited

FOREIGN PATENT DOCUMENTS

| | | | | |
|---|---|---|---|---|
| GB | 1314116 A | | 4/1973 | |
| GB | 2075539 A | | 11/1981 | |
| JP | 10-152636 | * | 6/1998 | ............ C09D 11/10 |
| JP | 2002-334869 A | | 11/2002 | |
| JP | 2003-300922 | * | 10/2003 | ............ C07C 39/12 |
| JP | 2004-177668 A | | 6/2004 | |
| JP | 2004-271838 A | | 9/2004 | |
| JP | 2005-250434 A | | 9/2005 | |
| JP | 2007-199653 | * | 8/2007 | ............... G03F 7/11 |
| JP | 2007-226170 A | | 9/2007 | |
| JP | 2007-226204 A | | 9/2007 | |
| JP | 2009-092691 | * | 4/2009 | ............... G03F 7/11 |
| JP | 2013-087173 | * | 5/2013 | ............ C08G 59/20 |
| WO | 2004/066377 A1 | | 8/2004 | |
| WO | 2007/097457 | * | 8/2007 | ............... G03F 7/11 |
| WO | 2009/072465 A1 | | 6/2009 | |
| WO | 2011/034062 A1 | | 3/2011 | |
| WO | 2015/080240 | * | 4/2015 | ........... C07D 311/92 |

OTHER PUBLICATIONS

International Search Report on Patentability for PCT/JP2016/057438 dated May 17, 2016; English translation submitted herewith (5 pages).
Sawicki, E. et al., Reaction of Thiaxanthydrol With Compounds Containing Active Hydrogen, Journal of Organic Chemistry, 1956, 21, pp. 183-189.

* cited by examiner

COMPOUND, RESIN, MATERIAL FOR FORMING UNDERLAYER FILM FOR LITHOGRAPHY, COMPOSITION FOR FORMING UNDERLAYER FILM FOR LITHOGRAPHY, UNDERLAYER FILM FOR LITHOGRAPHY, PATTERN FORMING METHOD, AND METHOD FOR PURIFYING COMPOUND OR RESIN

CROSS-REFERENCE TO RELATED APPLICATIONS

This application is a U.S. national phase application filed under 35 U.S.C. § 371 of International Application PCT/JP2016/057438, filed on Mar. 9, 2016, designating the United States, which claims priority from Japanese Application Number 2015-050731, filed Mar. 13, 2015, which are hereby incorporated herein by reference in their entirety.

FIELD OF THE INVENTION

The present invention relates to a compound or a resin having a specific structure. The present invention also relates to a material for forming an underlayer film for lithography and a composition for forming an underlayer film for lithography, containing the compound or the resin, an underlayer film for lithography, obtained from the material, and a photoresist pattern forming method using the material. Furthermore, the present invention relates to a method for purifying the compound or the resin.

BACKGROUND Of THE INVENTION

Semiconductor devices are manufactured through microfabrication by lithography using a photoresist material, but are required to be made finer by a pattern rule in accordance with the increase in integration degree and the increase in speed of LSI in recent years. In lithography using exposure to light, which is currently used as a general-purpose technique, the resolution is now approaching the intrinsic limitation associated with the wavelength of the light source.

A light source for lithography, for use in forming a resist pattern, has a shorter wavelength from a KrF excimer laser (248 nm) to an ArF excimer laser (193 nm). However, as the resist pattern is made finer and finer, there arise a problem of resolution and a problem of collapse of the resist pattern after development, and therefore there is demanded for making a resist film thinner. If the resist film is merely made thinner in response to such a demand, it is difficult to achieve the resist pattern having a film thickness sufficient for processing a substrate. Accordingly, there is increasingly required a process in which not only the resist pattern but also a resist underlayer film is prepared between a resist and a semiconductor substrate to be processed and the resist underlayer film is allowed to have a function as a mask at the time of processing the substrate.

Currently, as the resist underlayer film for such a process, various ones are known. Examples can include a resist underlayer film for lithography, having a selection ratio of dry etching rate close to the resist, unlike a conventional resist underlayer film having a high etching rate. As the material for forming such a resist underlayer film for lithography, there has been proposed a material for forming an underlayer film for multilayer resist process, containing a resin component having at least a substituent which releases a terminal group to form a sulfonic acid residue when a predetermined energy is applied, and a solvent (see, for example, Patent Literature 1). In addition, examples can also include a resist underlayer film for lithography, having a smaller selection ratio of dry etching rate than the resist. As the material for forming such a resist underlayer film for lithography, there has been proposed a resist underlayer film material including a polymer having a specific repeating unit (see, for example, Patent Literature 2). Furthermore, examples can include a resist underlayer film for lithography, having a smaller selection ratio of dry etching rate than the semiconductor substrate. As the material for forming such a resist underlayer film for lithography, there has been proposed a resist underlayer film material including a polymer formed by co-polymerizing a repeating unit of acenaphthylene, and a substituted or non-substituted repeating unit having a hydroxyl group (see, for example, Patent Literature 3).

On the other hand, as a material for allowing such a resist underlayer film to have a high etching resistance, an amorphous carbon underlayer film is well known, which is formed by CVD using methane gas, ethane gas, acetylene gas, or the like as a raw material. However, there is demanded, in terms of process, a resist underlayer film material that can form a resist underlayer film in a wet process such as a spin coating method or screen printing.

In addition, as a material that is excellent in optical characteristics and etching resistance and that is capable of being dissolved in a solvent and being applied to a wet process, the present inventors have proposed a composition for forming an underlayer film for lithography, which contains a naphthalene formaldehyde polymer including a specific constituent unit, and an organic solvent (see, for example, Patent Literatures 4 and 5).

Meanwhile, with respect to a forming method of an intermediate layer for use in forming a resist underlayer film in a three-layer process, for example, known are a forming method of a silicon nitride film (see, for example, Patent Literature 6), and a CVD forming method of a silicon nitride film (see, for example, Patent Literature 7). In addition, as an intermediate layer material for a three-layer process, known is a material containing a silsesquioxane-based silicon compound (see, for example, Patent Literatures 8 and 9).

CITATION LIST

Patent Literature

Patent Literature 1: Japanese Patent Laid-Open No. 2004-177668
Patent Literature 2: Japanese Patent Laid-Open No. 2004-271838
Patent Literature 3: Japanese Patent Laid-Open No. 2005-250434
Patent Literature 4: International Publication No. WO 2009/072465
Patent Literature 5: International Publication No. WO 2011/034062
Patent Literature 6: Japanese Patent Laid-Open No. 2002-334869
Patent Literature 7: International Publication No. WO 2004/066377
Patent Literature 8: Japanese Patent Laid-Open No. 2007-226170
Patent Literature 9: Japanese Patent Laid-Open No. 2007-226204

SUMMARY OF INVENTION

As described above, many materials for forming an underlayer film for lithography have been conventionally proposed, but there are no ones that not only have such a high solvent solubility as to be able to be applied to a wet process such as a spin coating method or screen printing, but also simultaneously satisfy heat resistance and etching resistance at a high level, and thus a new material is required to be developed.

In addition, in recent years, as the pattern has been increasingly made finer, there have been demanded step embedding properties which enable, even in the case of a substrate having a step (in particular, fine space, hole pattern and the like), a material to be filled uniformly in every part of the step, and flatness of a film formed. In particular, a resist layer disposed closer to a substrate (an underlayer film) is highly required to satisfy such demands.

The present invention has been made in view of the above problem, and an object thereof is to provide a compound, a resin, a material for forming an underlayer film for lithography, a composition including the material, a pattern forming method using the material, and a purification method of the compound or the resin, which can be applied to a wet process in formation of a photoresist underlayer film and which can provide an underlayer film for lithography, excellent in heat resistance and etching resistance.

The present inventors have intensively studied to solve the above problem, and as a result, have found that the above problem can be solved by using a compound or a resin having a specific structure, thereby leading to the completion of the present invention.

That is, the present invention is as follows.

[1]
A compound represented by the following formula (1):

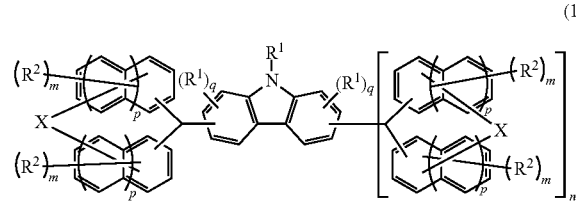

(1)

wherein each X independently represents an oxygen atom, a sulfur atom, or non-crosslinking, each $R^1$ is independently selected from the group consisting of a hydrogen atom, a halogen group, a nitro group, an amino group, a hydroxyl group, an alkyl group having 1 to 30 carbon atoms, an alkenyl group having 2 to 30 carbon atoms, an aryl group having 6 to 40 carbon atoms and combinations thereof, in which the alkyl group, the alkenyl group and the aryl group may have an ether bond, a ketone bond or an ester bond, each $R^2$ independently represents a linear, branched or cyclic alkyl group having 1 to 30 carbon atoms, an aryl group having 6 to 40 carbon atoms, an alkenyl group having 2 to 30 carbon atoms, a thiol group or a hydroxyl group, in which at least one $R^2$ represents a group having a hydroxyl group or a thiol group, each m is independently an integer of 1 to 7, each p is independently 0 or 1, each q is independently an integer of 0 to 4, and n is 0 or 1.

[2]
The compound according to [1], wherein the compound represented by the formula (1) is a compound represented by the following formula (1-1):

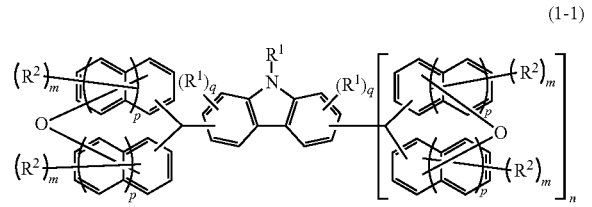

(1-1)

wherein $R^1$, $R^2$, m, p, q and n are the same as defined in the formula (1).

[3]
The compound according to [2], wherein the compound represented by the formula (1-1) is a compound represented by the following formula (1-2):

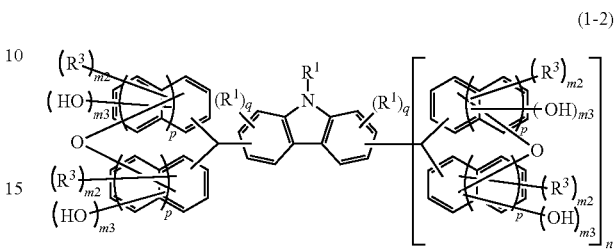

(1-2)

wherein $R^1$, p, q and n are the same as defined in the formula (1), each $R^3$ independently represents a linear, branched or cyclic alkyl group having 1 to 30 carbon atoms, an aryl group having 6 to 40 carbon atoms, or an alkenyl group having 2 to 30 carbon atoms, each $m^2$ is independently an integer of 0 to 5, each $m^3$ is independently an integer of 1 to 6, and $m^2+m^3$ is an integer of 1 to 6.

[4]
The compound according to [3], wherein the compound represented by the formula (1-2) is a compound represented by the following formula (1-3):

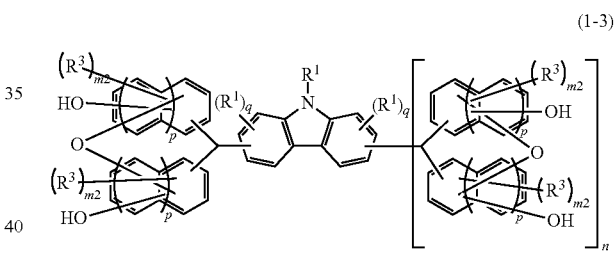

(1-3)

wherein $R^1$, p, q and n are the same as defined in the formula (1), and $R^3$ and $m^2$ are the same as defined in the formula (1-2).

[5]
The compound according to [4], wherein the compound represented by the formula (1-3) is a compound represented by the following formula (1-4):

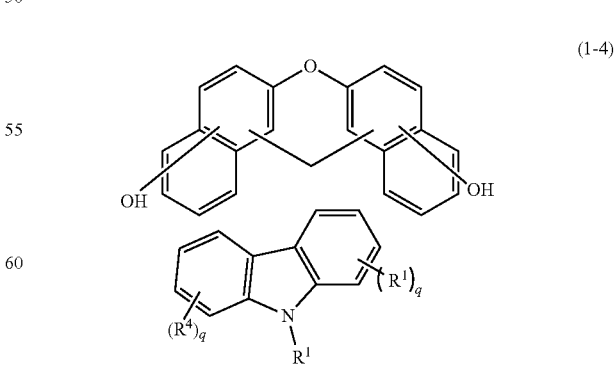

(1-4)

wherein $R^1$ and q are the same as defined in the formula (1).

[6]
The compound according to [5], wherein the compound represented by the formula (1-4) is a compound represented by the following formula (CAX-1).

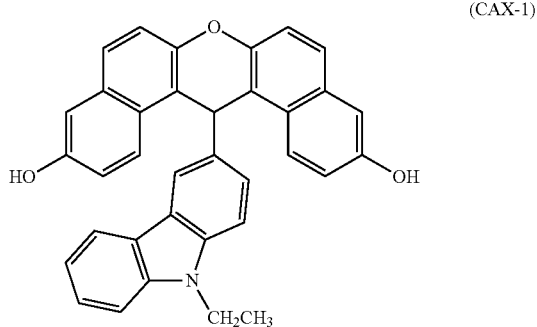 [SMILES: CCn1c2ccccc2c2cc(C3c4c(ccc5cc(O)ccc45)Oc4ccc5cc(O)ccc5c43)ccc21]

(CAX-1)

[7]
A resin obtained by using the compound according to any of [1] to [6] as a monomer.

[8]
The resin according to [7], obtained by reacting the compound according to any of [1] to [6] with a compound having crosslinking reactivity.

[9]
The resin according to [8], wherein the compound having crosslinking reactivity is one or more selected from the group consisting of aldehyde, ketone, carboxylic acid, carboxylic halide, a halogen-containing compound, an amino compound, an imino compound, isocyanate and an unsaturated hydrocarbon group-containing compound.

[10]
A resin having a structure represented by the following formula (2):

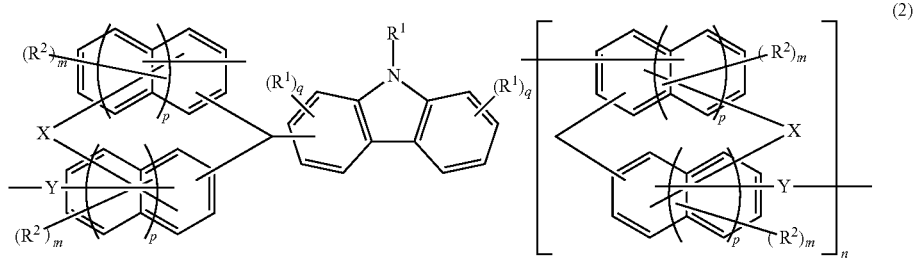

(2)

wherein each X independently represents an oxygen atom, a sulfur atom, or non-crosslinking, each $R^1$ is independently selected from the group consisting of a hydrogen atom, a halogen group, a nitro group, an amino group, a hydroxyl group, an alkyl group having 1 to 30 carbon atoms, an alkenyl group having 2 to 30 carbon atoms, an aryl group having 6 to 40 carbon atoms and combinations thereof, in which the alkyl group, the alkenyl group and the aryl group may have an ether bond, a ketone bond or an ester bond, each $R^2$ independently represents a linear, branched or cyclic alkyl group having 1 to 30 carbon atoms, an aryl group having 6 to 40 carbon atoms, an alkenyl group having 2 to 30 carbon atoms, a thiol group or a hydroxyl group, in which at least one $R^2$ represents a group having a hydroxyl group or a thiol group, each Y independently represents a single bond, or a linear or branched alkylene group having 1 to 20 carbon atoms, each m is independently an integer of 1 to 6, each p is independently 0 or 1, each q is independently an integer of 0 to 4, and n is 0 or 1.

[11]
A material for forming an underlayer film for lithography, comprising the compound according to any of [1] to [6] and/or the resin according to any of [7] to [10].

[12]
A composition for forming an underlayer film for lithography, comprising the material for forming the underlayer film for lithography according to [11], and a solvent.

[13]
The composition for forming the underlayer film for lithography according to [12], further comprising an acid generating agent.

[14]
The composition for forming the underlayer film for lithography according to [12] or [13], further comprising a crosslinking agent.

[15]
An underlayer film for lithography, formed from the composition for forming the underlayer film for lithography according to any of [12] to [14].

[16]
A resist pattern forming method comprising
step (A-1) of forming an underlayer film on a substrate by using the composition for forming the underlayer film for lithography according to any of [12] to [14],
step (A-2) of forming at least one photoresist layer on the underlayer film, and
step (A-3) of, after step (A-2), irradiating a predetermined region of the photoresist layer with radiation, followed by developing.

[17]
A circuit pattern forming method comprising
step (B-1) of forming an underlayer film on a substrate by using the composition for forming the underlayer film for lithography according to any of [12] to [14],
step (B-2) of forming an intermediate layer film on the underlayer film by using a silicon atom-containing resist intermediate layer film material,
step (B-3) of forming at least one photoresist layer on the intermediate layer film,
step (B-4) of, after step (B-3), irradiating a predetermined region of the photoresist layer with radiation, followed by developing to form a resist pattern, and
step (B-5) of, after step (B-4), etching the intermediate layer film with the resist pattern as a mask, etching the underlayer film with the obtained intermediate layer film pattern as an etching mask and etching the substrate with the obtained underlayer film pattern as an etching mask, to form a pattern on the substrate.

[18]
A method for purifying the compound according to any of [1] to [6] or the resin according to any of [7] to [10], the method comprising a step of bringing a solution comprising an organic solvent optionally immiscible with water and the compound or the resin into contact with an acidic aqueous solution for extraction.
[19]
The method according to [18], wherein the acidic aqueous solution is an aqueous solution of at least one mineral acid selected from the group consisting of hydrochloric acid, sulfuric acid, nitric acid and phosphoric acid, or an aqueous solution of at least one organic acid selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid and trifluoroacetic acid.
[20]
The method according to [18] or [19], wherein the organic solvent optionally immiscible with water is toluene, 2-heptanone, cyclohexanone, cyclopentanone, methyl isobutyl ketone, propylene glycol monomethyl ether acetate, 1,2-diethoxyketone, butyl acetate or ethyl acetate.
[21]
The method according to any of [18] to [20], further comprising a step of performing an extraction treatment with water, after the step of bringing the solution into contact with the acidic aqueous solution for extraction.

According to the present invention, it is possible to provide a material for forming an underlayer film for lithography, which can be applied to a wet process and which can provide an underlayer film for lithography, excellent in heat resistance and etching resistance.

DESCRIPTION OF EMBODIMENTS

Hereinafter, an embodiment (hereinafter, referred to as "the present embodiment") of the present invention will be described. It is to be noted that the present embodiments are illustrative for describing the present invention, and the present invention is not limited only to the present embodiments.
[Compound]
A compound of the present embodiment is represented by the following formula (1). The compound of the present embodiment has such a configuration, and therefore can be applied to a wet process in formation of a photoresist underlayer film and is excellent in heat resistance and etching resistance. In addition, the compound of the present embodiment has a specific structure, and therefore has a high heat resistance and also a high solvent solubility. Therefore, the compound of the present embodiment can be used to form an underlayer film whose degradation is suppressed at high-temperature baking, which is also excellent in etching resistance to oxygen plasma etching or the like, and which is excellent in embedding properties in a stepped substrate, and film flatness. Furthermore, the compound is also excellent in adhesiveness with a resist layer and therefore can form an excellent resist pattern.

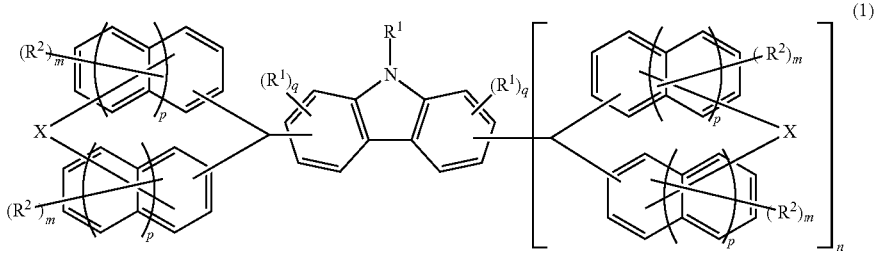

In the formula (1), each X independently represents an oxygen atom, a sulfur atom, or non-crosslinking.

Each $R^1$ is independently selected from the group consisting of a hydrogen atom, a halogen group, a nitro group, an amino group, a hydroxyl group, an alkyl group having 1 to 30 carbon atoms, an alkenyl group having 2 to 30 carbon atoms, an aryl group having 6 to 40 carbon atoms and combinations thereof, in which the alkyl group, the alkenyl group and the aryl group may have an ether bond, a ketone bond or an ester bond.

Examples of the halogen group include, but not limited to the following, a fluoro group, a chloro group, a bromo group and an iodo group.

Examples of the alkyl group having 1 to 30 carbon atoms include, but not limited to the following, a methyl group, an ethyl group, a n-propyl group, an i-propyl group, a cyclopropyl group, a n-butyl group, an i-butyl group, a s-butyl group, a t-butyl group, a cyclobutyl group, a 1-methyl-cyclopropyl group, a 2-methyl-cyclopropyl group, a n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, a cyclopentyl group, a 1-methyl-cyclobutyl group, a 2-methyl-cyclobutyl group, a 3-methyl-cyclobutyl group, a 1,2-dimethyl-cyclopropyl group, a 2,3-dimethyl-cyclopropyl group, a 1-ethyl-cyclopropyl group, a 2-ethyl-cyclopropyl group, a n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, a 1-ethyl-n-butyl group, a 2-ethyl-n-butyl group, a 1,1,2-trimethyl-n-propyl group, a 1,2,2-trimethyl-n-propyl group, a 1-ethyl-1-methyl-n-propyl group, a 1-ethyl-2-methyl-n-propyl group, a cyclohexyl group, a 1-methyl-cyclopentyl group, a 2-methyl-cyclopentyl group, a 3-methyl-cyclopentyl group, a 1-ethyl-cyclobutyl group, a 2-ethyl-cyclobutyl group, a 3-ethyl-cyclobutyl group, a 1,2-dimethyl-cyclobutyl group, a 1,3-dimethyl-cyclobutyl group, a 2,2-dimethyl-cyclobutyl group, a 2,3-dimethyl-cyclobutyl group, a 2,4-dimethyl-cyclobutyl group, a 3,3-dimethyl-cyclobutyl group, a 1-n-propyl-cyclopropyl group, a 2-n-propyl-cyclopropyl group, a 1-i-propyl-cyclopropyl group, a 2-i-propyl-cyclopropyl group, a 1,2,2-trimethyl-cyclopropyl group, a 1,2,3-trimethyl-cyclopropyl group, a 2,2,3-trimethyl-cyclopropyl group, a 1-ethyl-2-methyl-cyclopropyl group, a 2-ethyl-1-methyl-cyclopropyl group, 2-ethyl-2-methyl-cyclopropyl group and a 2-ethyl-3-methyl-cyclopropyl group.

Examples of the alkenyl group having 2 to 30 carbon atoms include, but not limited to the following, an ethenyl group, a 1-propenyl group, a 2-propenyl group, a 1-methyl-1-ethenyl group, a 1-butenyl group, a 2-butenyl group, a 3-butenyl group, a 2-methyl-1-propenyl group, a 2-methyl-2-propenyl group, a 1-ethylethenyl group, a 1-methyl-1-propenyl group, a 1-methyl-2-propenyl group, a 1-pentenyl group, a 2-pentenyl group, a 3-pentenyl group, a 4-pentenyl group, a 1-n-propylethenyl group, a 1-methyl-1-butenyl group, a 1-methyl-2-butenyl group, a 1-methyl-3-butenyl group, a 2-ethyl-2-propenyl group, a 2-methyl-1-butenyl group, a 2-methyl-2-butenyl group, a 2-methyl-3-butenyl group, a 3-methyl-1-butenyl group, a 3-methyl-2-butenyl group, a 3-methyl-3-butenyl group, a 1,1-dimethyl-2-propenyl group, a 1-i-propylethenyl group, a 1,2-dimethyl-1-propenyl group, a 1,2-dimethyl-2-propenyl group, a 1-cyclopentenyl group, a 2-cyclopentenyl group, a 3-cyclopentenyl group, a 1-hexenyl group, a 2-hexenyl group, a 3-hexenyl group, a 4-hexenyl group, 5-hexenyl group, a 1-methyl-1-pentenyl group, a 1-methyl-2-pentenyl group, a 1-methyl-3-pentenyl group, a 1-methyl-4-pentenyl group, a 1-n-butylethenyl group, a 2-methyl-1-pentenyl group, a 2-methyl-2-pentenyl group, a 2-methyl-3-pentenyl group, a 2-methyl-4-pentenyl group, a 2-n-propyl-2-propenyl group, a 3-methyl-1-pentenyl group, a 3-methyl-2-pentenyl group, a 3-methyl-3-pentenyl group, a 3-methyl-4-pentenyl group, a 3-ethyl-3-butenyl group, a 4-methyl-1-pentenyl group, a 4-methyl-2-pentenyl group, a 4-methyl-3-pentenyl group, a 4-methyl-4-pentenyl group, a 1,1-dimethyl-2-butenyl group, a 1,1-dimethyl-3-butenyl group, a 1,2-dimethyl-1-butenyl group, a 1,2-dimethyl-2-butenyl group, a 1,2-dimethyl-3-butenyl group, a 1-methyl-2-ethyl-2-propenyl group, a 1-s-butylethenyl group, a 1,3-dimethyl-1-butenyl group, a 1,3-dimethyl-2-butenyl group, a 1,3-dimethyl-3-butenyl group, a 1-i-butylethenyl group, a 2,2-dimethyl-3-butenyl group, a 2,3-dimethyl-1-butenyl group, a 2,3-dimethyl-2-butenyl group, a 2,3-dimethyl-3-butenyl group, a 2-i-propyl-2-propenyl group, a 3,3-dimethyl-1-butenyl group, a 1-ethyl-1-butenyl group, a 1-ethyl-2-butenyl group, a 1-ethyl-3-butenyl group, a 1-n-propyl-1-propenyl group, a 1-n-propyl-2-propenyl group, a 2-ethyl-1-butenyl group, a 2-ethyl-2-butenyl group, a 2-ethyl-3-butenyl group, a 1,1,2-trimethyl-2-propenyl group, a 1-t-butylethenyl group, a 1-methyl-1-ethyl-2-propenyl group, a 1-ethyl-2-methyl-1-propenyl group, a 1-ethyl-2-methyl-2-propenyl group, a 1-i-propyl-1-propenyl group, a 1-i-propyl-2-propenyl group, a 1-methyl-2-cyclopentenyl group, a 1-methyl-3-cyclopentenyl group, a 2-methyl-1-cyclopentenyl group, a 2-methyl-2-cyclopentenyl group, a 2-methyl-3-cyclopentenyl group, a 2-methyl-4-cyclopentenyl group, a 2-methyl-5-cyclopentenyl group, a 2-methylene-cyclopentyl group, a 3-methyl-1-cyclopentenyl group, a 3-methyl-2-cyclopentenyl group, a 3-methyl-3-cyclopentenyl group, a 3-methyl-4-cyclopentenyl group, a 3-methyl-5-cyclopentenyl group, a 3-methylene-cyclopentyl group, a 1-cyclohexenyl group, a 2-cyclohexenyl group and a 3-cyclohexenyl group.

Examples of the aryl group having 6 to 40 carbon atoms include, but not limited to the following, a phenyl group, an o-methylphenyl group, a m-methylphenyl group, a p-methylphenyl group, an o-chlorophenyl group, a m-chlorophenyl group, a p-chlorophenyl group, an o-fluorophenyl group, a p-fluorophenyl group, an o-methoxyphenyl group, a p-methoxyphenyl group, a p-nitrophenyl group, a p-cyanophenyl group, an α-naphthyl group, a β-naphthyl group, an o-biphenyl group, a m-biphenyl group, a p-biphenyl group, a 1-anthryl group, a 2-anthryl group, a 9-anthryl group, a 1-phenanthryl group, a 2-phenanthryl group, a 3-phenanthryl group, a 4-phenanthryl group and a 9-phenanthryl group.

Each $R^2$ independently represents a linear, branched or cyclic alkyl group having 1 to 30 carbon atoms, an aryl group having 6 to 30 carbon atoms, an alkenyl group having 2 to 30 carbon atoms, a thiol group or a hydroxyl group, in which at least one $R^2$ represents a group having a hydroxyl group or a thiol group. Herein, examples of the group having a hydroxyl group include, but not limited to the following, a hydroxyl group, a linear, branched or cyclic alkyl group having 1 to 30 carbon atoms, substituted with a hydroxyl group, an aryl group having 6 to 40 carbon atoms, substituted with a hydroxyl group, and an alkenyl group having 2 to 30 carbon atoms, substituted with a hydroxyl group. In addition, examples of the group having a thiol group include, but not limited to the following, a thiol group, a linear, branched or cyclic alkyl group having 1 to 30 carbon atoms, substituted with a thiol group, an aryl group having 6 to 40 carbon atoms, substituted with a thiol group, and an alkenyl group having 2 to 30 carbon atoms, substituted with a thiol group.

Examples of the alkyl group having 1 to 30 carbon atoms, the alkenyl group having 2 to 30 carbon atoms, and the aryl group having 6 to 40 carbon atoms include those exemplified with respect to $R^1$ described above.

Each m is independently an integer of 1 to 7, each p is independently 0 or 1, each q is independently an integer of 0 to 4, and n is 0 or 1.

The compound represented by the formula (1) has a high heat resistance due to rigidity of its structure while having a relatively low molecular weight, and therefore it can be used even under a high-temperature baking condition. In addition, the compound has a relatively low molecular weight and a low viscosity, and therefore, even when being applied to a substrate having a step (in particular, fine space, hole pattern and the like), it can be easily filled uniformly in every part of the step. As a result, a material for forming an underlayer film for lithography using such a compound can be improved in terms of embedding properties in a relatively advantageous manner. In addition, the compound imparts also a high etching resistance. Herein, the molecular weight of the compound of the present embodiment is preferably 400 to 3000, more preferably 400 to 2000, further preferably 400 to 1000. Herein, the molecular weight can be measured by a method in Examples described later.

In the compound represented by the formula (1), at least one $R^2$ has a hydroxyl group or a thiol group in terms of ease of crosslinking and solubility in an organic solvent.

The compound represented by the formula (1) is preferably a compound represented by the following formula (1-1) in terms of the supply of raw materials.

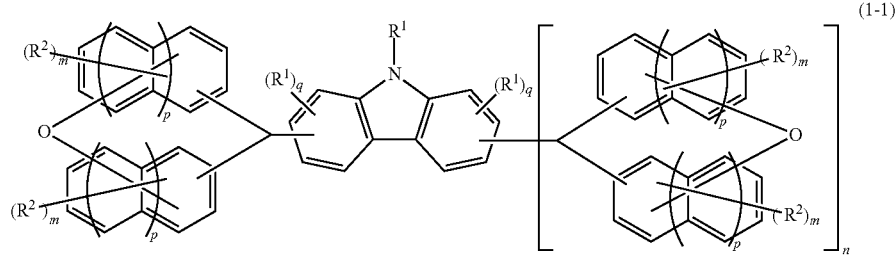

(1-1)

In the formula (1-1), $R^1$, $R^2$, m, p, q and n are the same as defined in the formula (1).

The compound represented by the formula (1-1) is more preferably a compound represented by the following formula (1-2) in terms of solubility in an organic solvent.

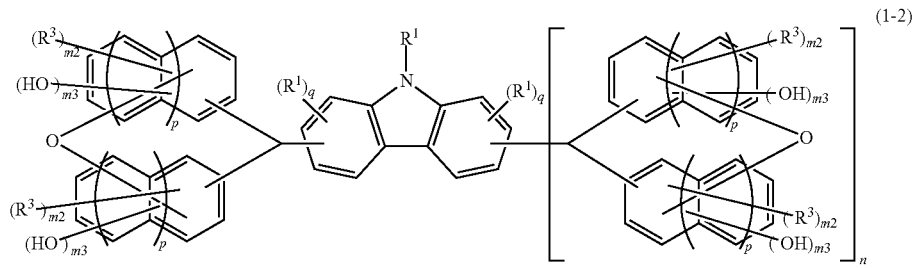

(1-2)

In the formula (1-2), $R^1$, p, q and n are the same as defined in the formula (1), each $R^3$ independently represents a linear, branched or cyclic alkyl group having 1 to 30 carbon atoms, an aryl group having 6 to 40 carbon atoms, or an alkenyl group having 2 to 30 carbon atoms, each $m^2$ is independently an integer of 0 to 5, each $m^3$ is independently an integer of 1 to 6, and $m^2+m^3$ is independently an integer of 1 to 6.

The compound represented by the formula (1-2) is further preferably a compound represented by the following formula (1-3) in terms of further solubility in an organic solvent.

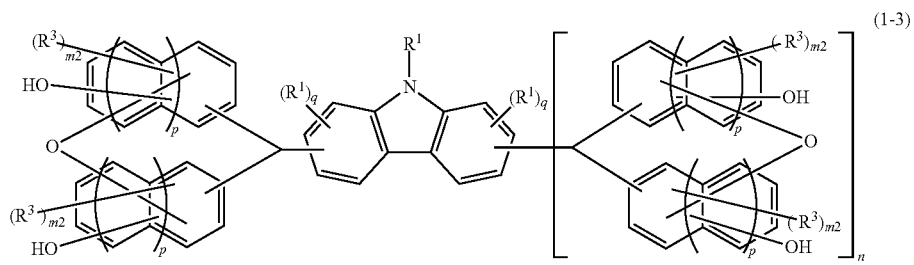

(1-3)

In the formula (1-3), $R^1$, $R^2$, p, q and n are the same as defined in the formula (1), and $R^3$ and $m^2$ are the same as defined in the formula (1-2).

The compound represented by the formula (1-3) is further more preferably a mode in which n=1 in the formula (1-3), namely, a compound represented by the following formula (1-4), from the viewpoint that one having a lower molecular weight is better in fluidity.

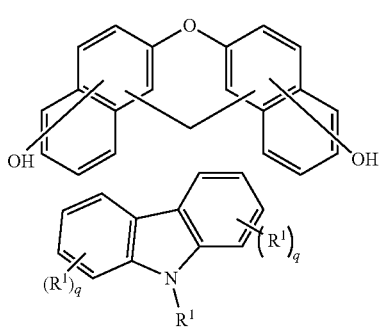

(1-4)

In the formula (1-4), $R^1$ and q are the same as defined in the formula (1).

Furthermore, the compound represented by the general formula (1-4) is further preferably a compound represented by the following formula (CAX-1) in terms of ease of production and the supply of raw materials.

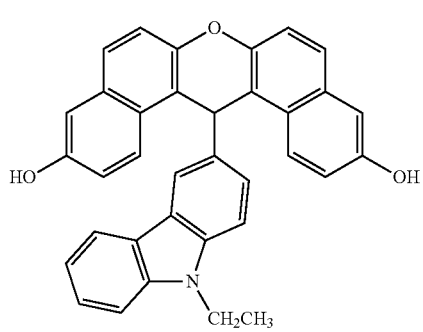

(CAX-1)

Hereinafter, specific examples of the compound represented by the formula (1) are shown, but are not limited to those recited herein.

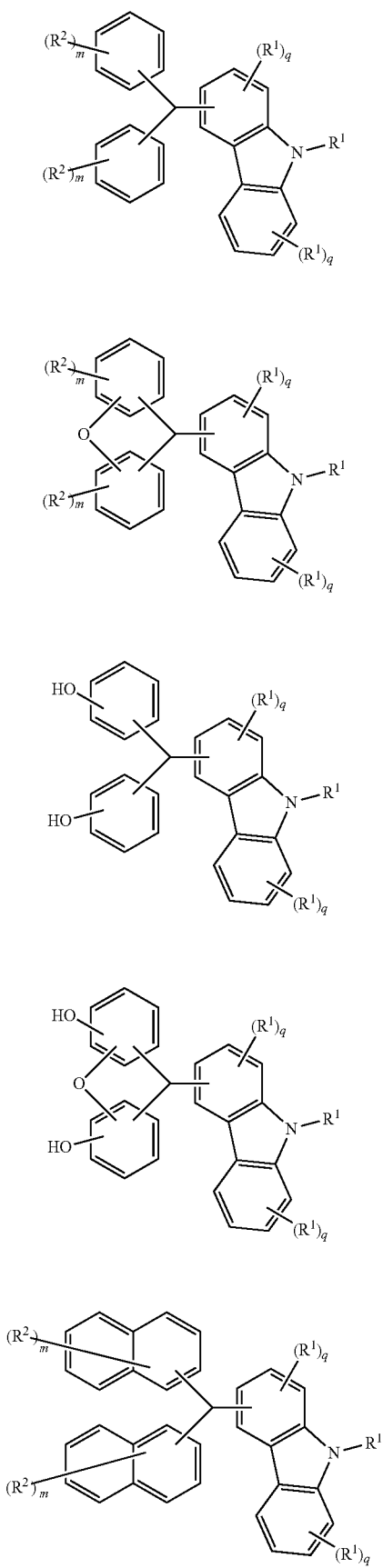
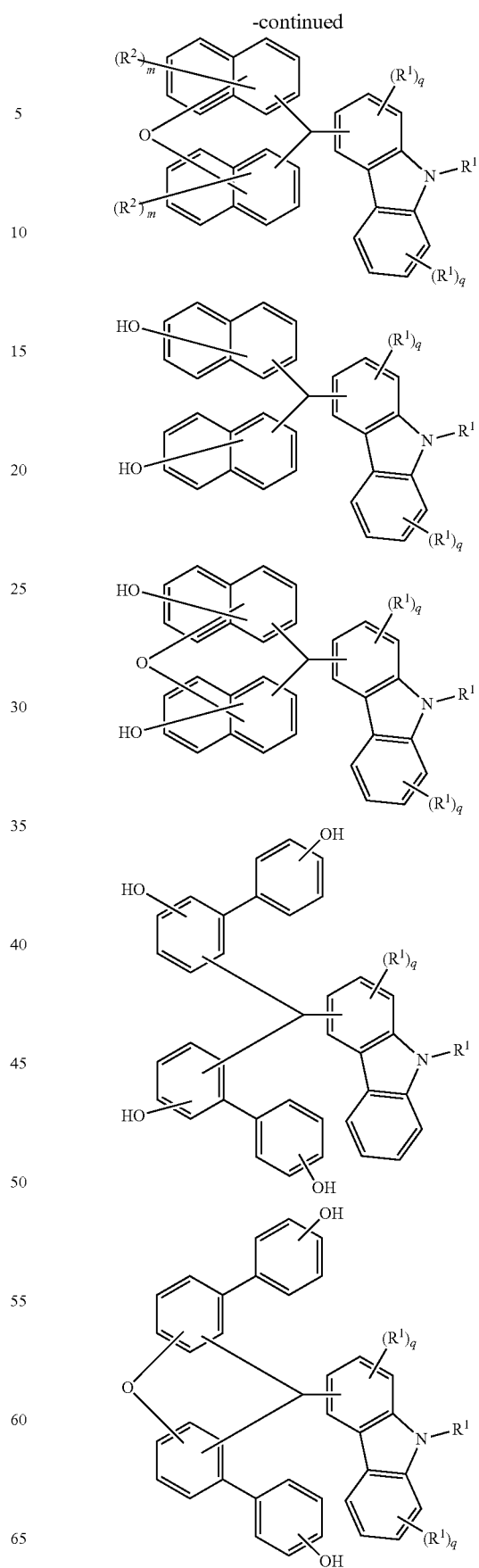

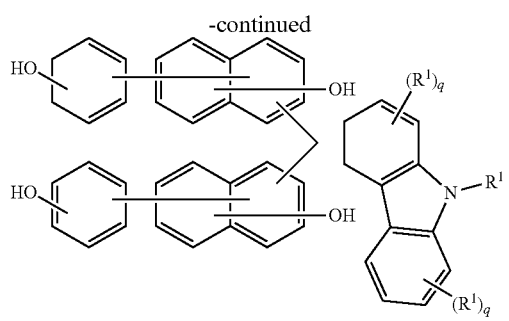
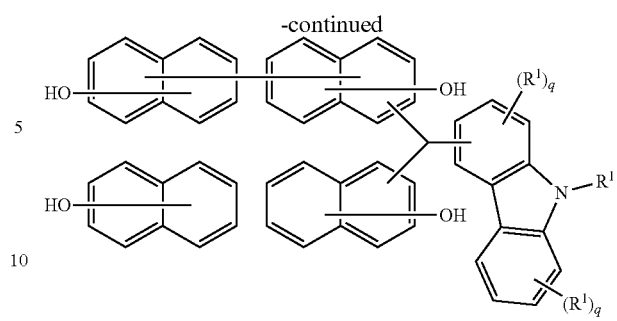
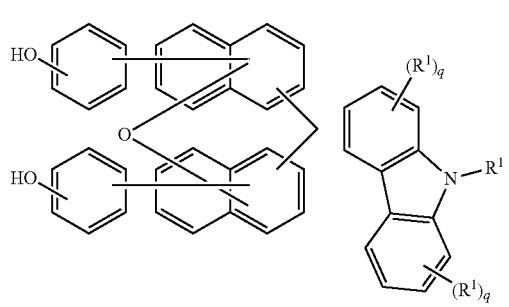
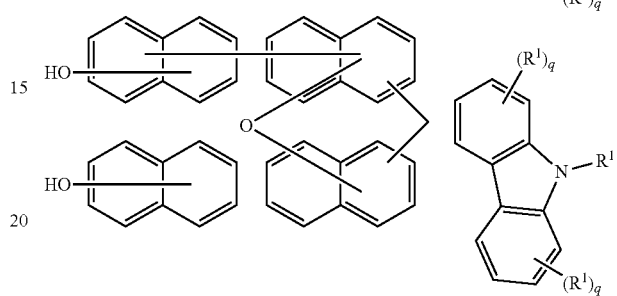
In the above compound, $R^1$, $R^2$, q and m are the same as defined in the formula (1).
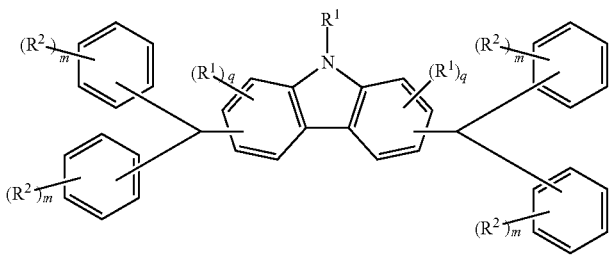
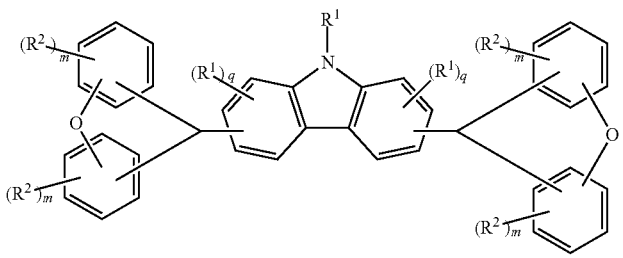
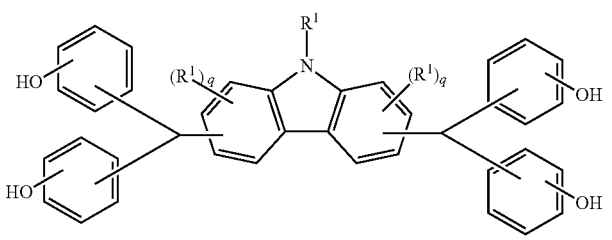
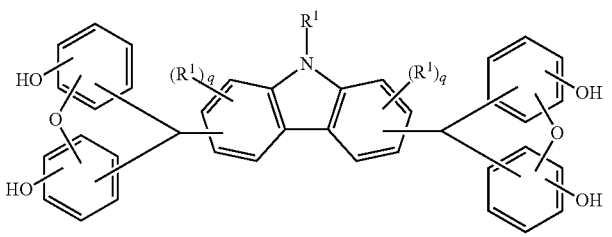

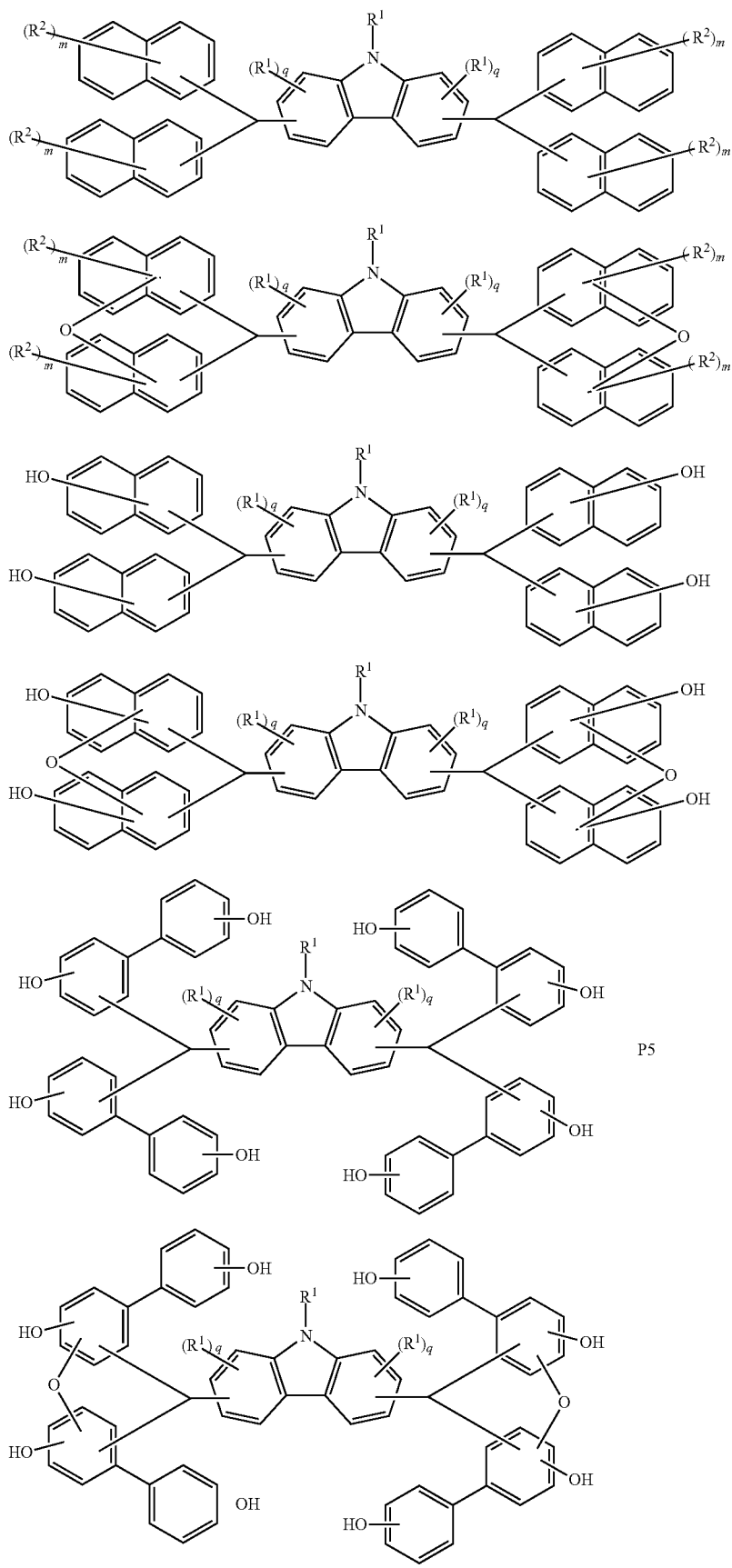

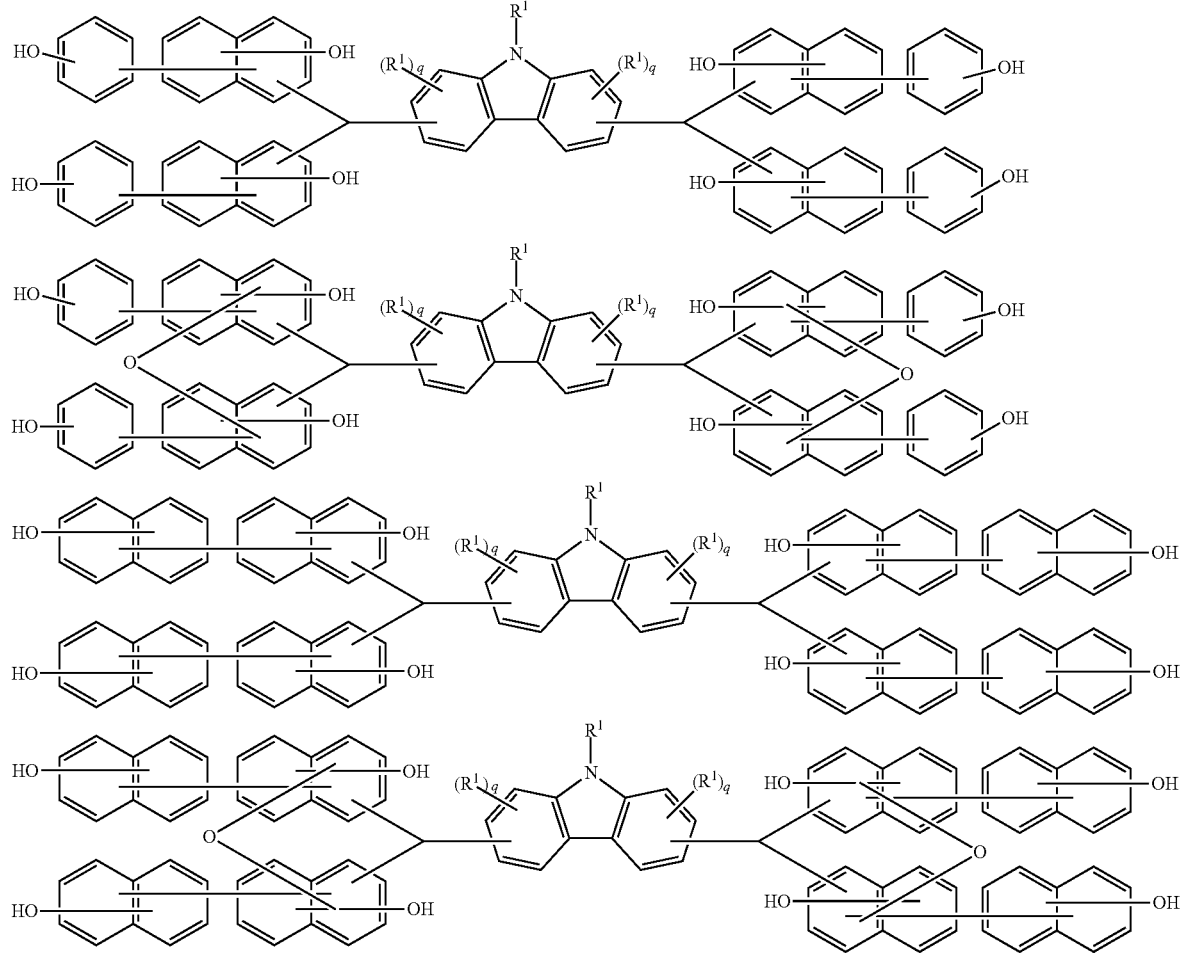

In the above compound, $R^1$, $R^2$ and m are the same as defined in the formula (1), and q is an integer of 0 to 3.

In the present embodiment, the compound represented by the formula (1) can be appropriately synthesized by applying a known method, and a synthesis method thereof is not particularly limited. For example, phenols, thiophenols, naphthols or thionaphthols and the corresponding aldehydes can be subjected to a polycondensation reaction under ordinary pressure in the presence of an acid catalyst to thereby provide the compound represented by the formula (1). The reaction can also be performed under pressure, if necessary.

Examples of the phenols include phenol, methyl phenol, methoxybenzene, catechol, hydroquinone and trimethylhydroquinone, but are not limited thereto. These can be used singly or in combinations of two or more thereof. Among them, hydroquinone and trimethylhydroquinone are preferably used from the viewpoint that a xanthene structure can be easily made.

Examples of the thiophenols include benzenethiol, methylbenzenethiol, methoxybenzenethiol, benzenedithiol and trimethylbenzenedithiol, but are not limited thereto. These can be used singly or in combinations of two or more thereof. Among them, benzenedithiol and trimethylbenzenedithiol are preferably used from the viewpoint that a thioxanthene structure can be easily made.

Examples of the naphthols include naphthol, methylnaphthol, methoxynaphthol and naphthalenediol, but are not limited thereto. These can be used singly or in combinations of two or more thereof. Among them, naphthalenediol is preferably used from the viewpoint that a benzoxanthene structure can be easily made.

Examples of the thionaphthols include naphthalenethiol, methylnaphthalenethiol, methoxynaphthalenethiol and naphthalenedithiol, but are not limited thereto. These can be used singly or in combinations of two or more thereof. Among them, naphthalenedithiol is preferably used from the viewpoint that a thiobenzoxanthene structure can be easily made.

Examples of the aldehydes include carbazole-3-carbaldehyde, N-methylcarbazole-3-carbaldehyde, N-ethylcarbazole-3-carbaldehyde, N-propylcarbazole-3-carbaldehyde, N-(t-butyl)carbazole-3-carbaldehyde, N-hydroxyethylcarbazole-3-carbaldehyde, N-cyclohexylcarbazole-3-carbaldehyde, N-phenylcarbazole-3-carbaldehyde, N-(4-methylphenyl)carbazole-3-carbaldehyde, N-(4-ethylphenyl)carbazole-3-carbaldehyde, N-(4-methoxyphenyl)carbazole-3-carbaldehyde, N-(3-methoxyphenyl)carbazole-3-carbaldehyde, N-(4-ethoxyphenyl)carbazole-3-carbaldehyde, N-(3-ethoxyphenyl)carbazole-3-carbaldehyde, N-(4-hydroxyphenyl)carbazole-3-carbaldehyde, N-(3-hydroxyphenyl)carbazole-3-carbaldehyde, N-benzylcarbazole-3-carbaldehyde, N-biphenylcarbazole-3-carbaldehyde, N-(4-hydroxybiphenyl)carbazole-3-carbaldehyde, 1,4-dimethyl-9H-carbazole-3-carbaldehyde, 6-methoxy-1,4-dimethyl-9H-carbazole-3-carbaldehyde, N-nitrosocarbazole-3-carbaldehyde, carbazole-3,6-dicarbaldehyde, N-methylcarbazole-3,6-dicarbaldehyde, N-ethylcarbazole-3,6-dicarbaldehyde, N-propylcarbazole-3,6-dicarbaldehyde, N-(t-butyl)carbazole-3,6-dicarbaldehyde, N-hydroxyethylcarbazole-3,6-dicarbaldehyde, N-cyclohexylcarbazole-3,6-dicarbaldehyde, N-phenylcarbazole-3,6-dicarbaldehyde, N-(4-methylphenyl)carbazole-3,6-dicarbaldehyde, N-(4-ethylphenyl)carbazole-3,6-dicarbaldehyde, N-(4-methoxyphenyl)carbazole-3,6-dicarbaldehyde, N-(3-methoxyphenyl)carbazole-3,6-dicarbaldehyde, N-(4-ethoxyphenyl)carbazole-3,6-dicarbaldehyde, N-(3-ethoxyphenyl)carbazole-3,6-dicarbaldehyde, N-(4-hydroxyphenyl)carbazole-3,6-dicarbaldehyde, N-(3-hydroxyphenyl)carbazole-3,6-dicarbaldehyde, N-benzylcarbazole-3,6-dicarbaldehyde, N-biphenylcarbazole-3,6-dicarbaldehyde, N-(4-hydroxybiphenyl)carbazole-3,6-dicarbaldehyde, 1,4-dimethyl-9H-carbazole-3,6-dicarbaldehyde and N-nitrosocarbazole-3,6-dicarbaldehyde, but are not limited thereto. These can be used singly or in combinations of two or more thereof. Among them, N-ethylcarbazole-3-carbaldehyde and N-hydroxyethylcarbazole-3-carbaldehyde are preferably used from the viewpoint of imparting a high solubility and a high heat resistance.

The acid catalyst for use in the above reaction can be appropriately selected from known ones and used, and is not particularly limited. Such an acid catalyst is an inorganic acid or an organic acid, as widely known, and examples thereof include inorganic acids such as hydrochloric acid, sulfuric acid, phosphoric acid, hydrobromic acid, or hydrofluoric acid, organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, or naphthalenedisulfonic acid, Lewis acids such as zinc chloride, aluminum chloride, iron chloride, or boron trifluoride, or solid acids such as tungstosilicic acid, tungstophosphoric acid, silicomolybdic acid, or phosphomolybdic acid, but are not limited thereto. Among them, organic acids and solid acids are preferable in terms of production, and hydrochloric acid or sulfuric acid is more preferably used in terms of production such as availability or handleability. Herein, these acid catalysts can be used alone, or two or more thereof can be used in combination. In addition, the amount of the acid catalyst to be used can be appropriately set depending on the types of raw materials to be used and the catalyst to be used, reaction conditions, and the like, and is not particularly limited, but the amount is preferably 0.01 to 100 parts by mass based on 100 parts by mass of reaction raw materials.

A reaction solvent may also be used during the above reaction. The reaction solvent that can be used is not particularly limited and is appropriately selected from known ones, as long as the reaction of the aldehydes to be used and the phenols, thiophenols, naphthols or thionaphthols to be used progresses, and examples thereof include water, methanol, ethanol, propanol, butanol, tetrahydrofuran, dioxane, ethylene glycol dimethyl ether, ethylene glycol diethyl ether, or a mixed solvent thereof. Herein, these solvents can be used alone, or two or more thereof can be used in combination. In addition, the amount of the solvent to be used can be appropriately set depending on the types of raw materials to be used and the catalyst to be used, reaction conditions, and the like, and is not particularly limited, but the amount is preferably 0 to 2000 parts by mass based on 100 parts by mass of reaction raw materials. Furthermore, the reaction temperature in the above reaction can be appropriately selected depending on the reactivity of reaction raw materials, and is not particularly limited, but the reaction temperature usually ranges from 10 to 200° C.

In order to obtain the compound represented by the general formula (1) of the present embodiment, the reaction temperature is preferably high and, specifically, preferably ranges from 60 to 200° C. Herein, the reaction method that can be used is appropriately selected from known methods, and is not particularly limited, but includes a method in which the phenols, thiophenols, naphthols or thionaphthols, the aldehydes, and the catalyst are charged at once, and a method in which the phenols, thiophenols, naphthols or thionaphthols, and the aldehydes or ketones are dropped in the presence of the catalyst. After completion of the polycondensation reaction, the resulting compound can be isolated according to an ordinary method, and the isolation method is not particularly limited. For example, in order to remove the unreacted raw materials and the catalyst present in the system, a common method in which the temperature in a reaction tank is raised to 130 to 230° C. to remove a volatile content at about 1 to 50 mmHg can be adopted to thereby provide an objective compound.

The reaction progresses under a preferable reaction condition in which 1 mol to an excess amount of the phenols, thiophenols, naphthols or thionaphthols and 0.001 to 1 mol of the acid catalyst are used based on 1 mol of the aldehydes at ordinary pressure and at 50 to 150° C. for about 20 minutes to 100 hours.

After completion of the reaction, the objective compound can be isolated by a known method. For example, the objective compound, the compound represented by the general formula (1), can be obtained by concentrating a reaction liquid, adding pure water thereto to precipitate a reaction product, cooling the resultant to room temperature followed by filtration for separation, drying a solid obtained by filtration, then separating the solid into the reaction product and a by-product for purification by column chromatography, and performing distilling off of the solvent, filtration and drying.

[Resin]

A resin of the present embodiment is a resin obtained by using the compound represented by the formula (1) as a monomer. The resin of the present embodiment has a structure represented by formula (2).

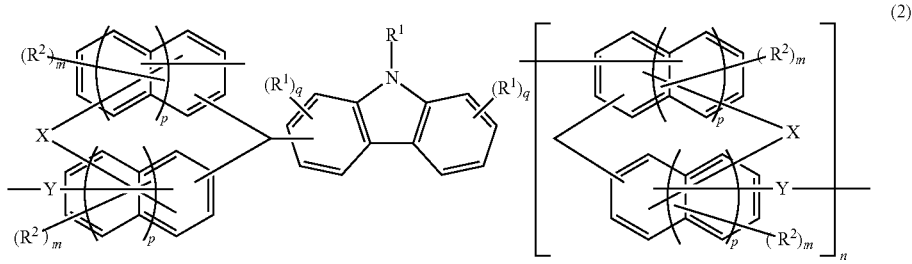

In formula (2), each X independently represents an oxygen atom, a sulfur atom, or non-crosslinking.

Each $R^1$ is independently selected from the group consisting of a hydrogen atom, a halogen group, a nitro group, an amino group, a hydroxyl group, an alkyl group having 1 to 30 carbon atoms, an alkenyl group having 2 to 30 carbon atoms, an aryl group having 6 to 40 carbon atoms and combinations thereof, in which the alkyl group, the alkenyl group and the aryl group may have an ether bond, a ketone bond or an ester bond.

Each $R^2$ independently represents a linear, branched or cyclic alkyl group having 1 to 30 carbon atoms, an aryl group having 6 to 40 carbon atoms, an alkenyl group having 2 to 30 carbon atoms, a thiol group or a hydroxyl group, in which at least one $R^2$ represents a group having a hydroxyl group or a thiol group. Herein, examples of the group having a hydroxyl group include, but not limited to the following, a hydroxyl group, a linear, branched or cyclic alkyl group having 1 to 30 carbon atoms, substituted with a hydroxyl group, an aryl group having 6 to 40 carbon atoms, substituted with a hydroxyl group, and an alkenyl group having 2 to 30 carbon atoms, substituted with a hydroxyl group. In addition, examples of the group having a thiol group include, but not limited to the following, a thiol group, a linear, branched or cyclic alkyl group having 1 to 30 carbon atoms, substituted with a thiol group, an aryl group having 6 to 40 carbon atoms, substituted with a thiol group, and an alkenyl group having 2 to 30 carbon atoms, substituted with a thiol group.

Each Y independently represents a single bond, or a linear or branched alkylene group having 1 to 20 carbon atoms.

Each m is independently an integer of 1 to 6, each p is independently 0 or 1, each q is independently an integer of 0 to 4, and n is 0 or 1.

The resin having the structure represented by formula (2), to be used in the present embodiment, is obtained by, for example, reacting the compound represented by the formula (1) with a compound having crosslinking reactivity.

The compound having crosslinking reactivity is not particularly limited as long as it can provide an oligomer or a polymer of the compound represented by the formula (1), and known one can be used therefor. Specific examples thereof include, for example, aldehyde, ketone, carboxylic acid, carboxylic halide, a halogen-containing compound, an amino compound, an imino compound, isocyanate, and an unsaturated hydrocarbon group-containing compound, but are not limited thereto.

Specific examples of the resin having the structure represented by formula (2) include, but not limited to the following, a novolac resin obtained by a condensation reaction of the compound represented by the formula (1) with an aldehyde as the monomer having crosslinking reactivity.

Herein, examples of the aldehyde for use in forming the novolac resin of the compound represented by the formula (1) include formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarbaldehyde, phenanthrenecarbaldehyde, pyrenecarbaldehyde, and furfural, but are not limited thereto. Among them, formaldehyde is more preferable. Herein, these aldehydes can be used alone, or two or more thereof can be used in combination. In addition, the amount of the aldehydes to be used is not particularly limited, but the amount is preferably 0.2 to 5 mol and more preferably 0.5 to 2 mol, based on 1 mol of the compound represented by the formula (1).

A reaction solvent can also be used in a condensation reaction of the compound represented by the formula (1) and the aldehyde. The reaction solvent that can be used in the polycondensation is not particularly limited and is appropriately selected from known ones, and examples thereof include water, methanol, ethanol, propanol, butanol, tetrahydrofuran, dioxane, or a mixed solvent thereof. Herein, these solvents can be used alone, or two or more thereof can be used in combination.

In addition, the amount of the solvent to be used can be appropriately set depending on the types of raw materials to be used and the catalyst to be used, reaction conditions, and the like, and is not particularly limited, but the amount preferably ranges from 0 to 2000 parts by mass based on 100 parts by mass of reaction raw materials. Furthermore, the reaction temperature can be appropriately selected depending on the reactivity of reaction raw materials, and is not particularly limited, but the reaction temperature usually ranges from 10 to 200° C. Herein, the reaction method that can be used is appropriately selected from known methods, and is not particularly limited, but includes a method in which the compound represented by the formula (1), the aldehydes, and the catalyst are charged at once, and a method in which the compound represented by the formula (1) and the aldehydes are dropped in the presence of the catalyst.

After completion of the polycondensation reaction, the resulting compound can be isolated according to an ordinary method, and the isolation method is not particularly limited. For example, in order to remove the unreacted raw materials and the catalyst present in the system, a common method in which the temperature in a reaction tank is raised to 130 to 230° C. to remove a volatile content at about 1 to 50 mmHg can be adopted to thereby provide an objective novolac resin.

Herein, the resin of the present embodiment may be a homopolymer of the compound represented by the formula (1), or may be a copolymer thereof with other phenols. Examples of the copolymerizable phenols include phenol, cresol, dimethylphenol, trimethylphenol, butylphenol, phenylphenol, diphenylphenol, naphthylphenol, resorcinol, methylresorcinol, catechol, butylcatechol, methoxyphenol, methoxyphenol, propylphenol, pyrogallol, and thymol, but are not limited thereto.

In addition, the resin of the present embodiment may be one obtained by copolymerization with a polymerizable monomer other than the above-described other phenols. Examples of such a copolymerizable monomer include naphthol, methylnaphthol, methoxynaphthol, dihydroxynaphthalene, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, vinylnorbornaene, pinene, and limonene, but are not limited thereto. Herein, the resin of the present embodiment may be a bi or higher functional (for example, bi to tetra) copolymer of the compound represented by the formula (1) with the above-described phenols, may be a bi or higher functional (for example, bi to tetra) copolymer of the compound represented by the formula (1) with the above-described copolymerizable monomer, or may be a ter or higher (for example, ter to tetra) copolymer of the compound represented by the formula (1), the above-described phenols, and the above-described copolymerizable monomer.

Herein, the molecular weight of the resin of the present embodiment is not particularly limited, and the weight average molecular weight (Mw) in terms of polystyrene is preferably 500 to 20,000, and more preferably 750 to 10,000. In addition, the resin of the present embodiment preferably has a dispersity (weight average molecular weight Mw/number average molecular weight Mn) in a range from 1.1 to 7 from the viewpoints of improving a crosslinking efficiency and suppressing a volatile component during baking. Herein, the Mn can be determined by a method in Examples described later.

The compound represented by the formula (1) and/or the resin obtained by using the compound as a monomer preferably have/has a high solubility in the solvent from the viewpoint of making the application of a wet process easier. More specifically, when the solvent is 1-methoxy-2-propanol (PGME) and/or propylene glycol monomethyl ether acetate (PGMEA), such a compound and/or resin preferably have/has a solubility of 10% by mass or more in the solvent. Herein, the solubility in PGME and/or PGMEA is defined as "Mass of resin/(Mass of resin+Mass of solvent)×100 (% by mass)". For example, in the case where 10 g of the compound represented by the formula (1) and/or the resin obtained by using the compound as a monomer are/is evaluated to be dissolved in 90 g of PGMEA, the solubility of the compound represented by the formula (1) and/or the resin obtained by using the compound as a monomer in PGMEA is "10% by mass or more", and in the case where the compound and/or the resin are/is evaluated not to be dissolved, the solubility is "less than 10% by mass".

[Material for Forming Underlayer Film for Lithography]

A material for forming an underlayer film for lithography of the present embodiment contains at least one substance selected from the group consisting of the compound represented by the formula (1) and the resin obtained by using the compound as a monomer. In the present embodiment, the content of the substance in the material for forming an underlayer film for lithography is preferably 1 to 100% by mass, more preferably 10 to 100% by mass, further preferably 50 to 100% by mass, further more preferably 100% by mass in terms of coatability and quality stability.

Herein, the material for forming an underlayer film for lithography of the present embodiment may include a known material for forming an underlayer film for lithography, or the like as long as the effect of the present embodiment is not impaired.

As described above, the material for forming an underlayer film for lithography of the present embodiment contains at least the compound or the resin of the present embodiment. The material for forming an underlayer film for lithography of the present embodiment has such a configuration, and therefore can be applied to a wet process and is excellent in heat resistance and etching resistance. Furthermore, since the material for forming an underlayer film for lithography of the present embodiment is formed using the compound or the resin, the material can be used to form an underlayer film whose degradation is suppressed at high-temperature baking and which is also excellent in etching resistance to oxygen plasma etching or the like. Furthermore, the material for forming an underlayer film for lithography of the present embodiment is also excellent in adhesiveness with a resist layer and therefore can form an excellent resist pattern.

[Composition for Forming Underlayer Film for Lithography]

A composition for forming an underlayer film for lithography of the present embodiment contains a solvent other than the compound represented by the formula (1) and/or the resin obtained by using the compound as a monomer. The composition for forming an underlayer film for lithography of the present embodiment may contain, if necessary, a crosslinking agent, an acid generating agent, and other component. Hereinafter, the solvent and these optional components will be described.

[Solvent]

The composition for forming an underlayer film for lithography of the present embodiment may contain a solvent. The solvent is not particularly limited and a known solvent can be appropriately used as long as it dissolves at least the compound represented by the formula (1) and/or the resin obtained by using the compound as a monomer.

Specific examples of the solvent include ketone-based solvents such as acetone, methyl ethyl ketone, methyl isobutyl ketone and cyclohexanone; cellosolve-based solvents such as propylene glycol monomethyl ether and propylene glycol monomethyl ether acetate; ester-based solvents such as ethyl lactate, methyl acetate, ethyl acetate, butyl acetate, isoamyl acetate, ethyl lactate, methyl methoxypropionate and methyl hydroxyisobutyrate; alcohol-based solvents such as methanol, ethanol, isopropanol and 1-ethoxy-2-propanol; and aromatic hydrocarbons such as toluene, xylene and anisole, but are not limited thereto. These solvents can be used singly or in combinations of two or more thereof.

Among the solvents, preferable are cyclohexanone, propylene glycol monomethyl ether, propylene glycol monomethyl ether acetate, ethyl lactate, methyl hydroxyisobutyrate, and anisole, in terms of safety.

The content of the solvent is not particularly limited, but it is preferably 100 to 10,000 parts by mass, more preferably 200 to 5,000 parts by mass, further preferably 200 to 1,000 parts by mass, based on 100 parts by mass of the material for forming an underlayer film, in terms of solubility and film formation.

[Crosslinking Agent]

The composition for forming an underlayer film for lithography of the present embodiment may contain, if necessary, a crosslinking agent from the viewpoint of suppression of intermixing, and the like. Specific examples of the crosslinking agent usable in the present embodiment include a melamine compound, a guanamine compound, a glycoluril compound, a urea compound, an epoxy compound, a thioepoxy compound, an isocyanate compound, an azide compound, and a compound including a double bond such as an alkenyl ether group, these compounds being substituted with at least one group selected from a methylol group, an alkoxymethyl group and an acyloxymethyl group, as a substituent (crosslinkable group), but are not limited thereto. Herein, these crosslinking agents can be used singly or in combinations of two or more thereof. Such a crosslinking agent can also be used as an additive. Herein, the crosslinkable group may also be introduced as a pendant group into a polymer side chain of the compound represented by the formula (1) and/or the resin obtained by using the compound as a monomer. A compound including a hydroxyl group can also be used as the crosslinking agent.

Specific examples of the melamine compound include, but are not limited to the following, hexamethylolmelamine, hexamethoxymethylmelamine, a compound in which 1 to 6 methylol groups in hexamethylolmelamine are methoxymethylated, or mixtures thereof, and hexamethoxyethylmelamine, hexaacyloxymethylmelamine, a compound in which 1 to 6 methylol groups in hexamethylolmelamine are acyloxymethylated, or mixtures thereof. Specific examples of the epoxy compound include, but are not limited to the following, tris(2,3-epoxypropyl)isocyanurate, trimethylolmethane triglycidyl ether, trimethylolpropane triglycidyl ether, and triethylolethane triglycidyl ether.

Specific examples of the guanamine compound include, but are not limited to the following, tetramethylolguanamine, tetramethoxymethylguanamine, a compound in which 1 to 4 methylol groups in tetramethylolguanamine are methoxymethylated, or mixtures thereof, and tetramethoxyethylguanamine, tetraacyloxyguanamine, a compound in which 1 to 4 methylol groups in tetramethylolguanamine are acyloxymethylated, or mixtures thereof. Specific examples of the glycoluril compound include, but are not limited to the following, tetramethylolglycoluril, tetramethoxyglycoluril, tetramethoxymethylglycoluril, a compound in which 1 to 4 methylol groups in tetramethylolglycoluril are methoxymethylated, or mixtures thereof, and a compound in which 1 to 4 methylol groups in tetramethylolglycoluril are acyloxymethylated, or mixtures thereof. Specific examples of the urea compound include, but are not limited to the following, tetramethylolurea, tetramethoxymethylurea, a compound in which 1 to 4 methylol groups in tetramethylolurea are methoxymethylated, or mixtures thereof, and tetramethoxyethylurea.

Specific examples of the compound including an alkenyl ether group include, but are not limited to the following, ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

In the composition for forming an underlayer film for lithography of the present embodiment, the content of the crosslinking agent is not particularly limited, but the content is preferably 5 to 50 parts by mass, more preferably 10 to 40 parts by mass, based on 100 parts by mass of the material for forming an underlayer film for lithography. The content is set within the above preferable range to result in tendencies to suppress the occurrence of the mixing phenomenon with the resist layer, and to result in tendencies to enhance an antireflective effect and improve film formability after crosslinking.

[Acid Generating Agent]

The composition for forming an underlayer film for lithography of the present embodiment may also contain, if necessary, an acid generating agent from the viewpoint of further promoting a crosslinking reaction by heat. As the acid generating agent, one for generating an acid by pyrolysis and one for generating an acid by light irradiation are known, and any of them can be used.

Examples of the acid generating agent include:
1) an onium salt of the following general formula (P1a-1), (P1a-2), (P1a-3) or (P1b),
2) a diazomethane derivative of the following general formula (P2),
3) a glyoxime derivative of the following general formula (P3),
4) a bissulfone derivative of the following general formula (P4),
5) a sulfonic acid ester of an N-hydroxyimide compound of the following general formula (P5),
6) a β-ketosulfonic acid derivative,
7) a disulfone derivative,
8) a nitrobenzylsulfonate derivative, and
9) a sulfonic acid ester derivative, but are not limited thereto. Herein, these acid generating agents can be used alone, or two or more thereof can be used in combination.

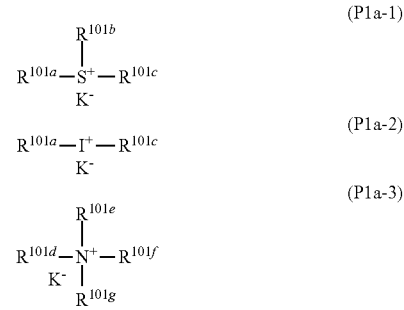

In the above formulae, each of $R^{101a}$, $R^{101b}$ and $R^{101c}$ independently represents a linear, branched or cyclic alkyl group, alkenyl group, oxoalkyl group or oxoalkenyl group having 1 to 12 carbon atoms; an aryl group having 6 to 20 carbon atoms; or an aralkyl group or aryloxyalkyl group having 7 to 12 carbon atoms, and a part or all of hydrogen atoms of these groups may be substituted with an alkoxy group or the like. In addition, $R^{101b}$ and $R^{101c}$ may form a ring, and if forming a ring, each of $R^{101b}$ and $R^{101c}$ independently represents an alkylene group having 1 to 6 carbon atoms. $K^-$ represents a non-nucleophilic counter ion. $R^{101d}$, $R^{101e}$, $R^{101f}$ and $R^{101g}$ are represented by each independently adding a hydrogen atom to $R^{101a}$, $R^{101b}$ and $R^{101c}$. $R^{101d}$ and $R^{101e}$, and $R^{101d}$, $R^{101e}$, and $R^{101f}$ may form a ring, and if forming a ring, $R^{101d}$ and $R^{101e}$, and $R^{101d}$, $R^{101e}$ and $R^{101f}$ represent an alkylene group having 3 to 10 carbon atoms, or a heteroaromatic ring having therein the nitrogen atom(s) in the formula.

$R^{101a}$, $R^{101b}$, $R^{101c}$, $R^{101d}$, $R^{101e}$, $R^{101f}$ and $R^{101g}$ described above may be the same or different from one another. Specifically, examples of the alkyl group include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methyl cyclohexyl group, a cyclohexylmethyl group, a norbornyl group, and an adamantyl group. Examples of the alkenyl group include, but are not limited to the following, a vinyl group, an allyl group, a propenyl group, a butenyl group, a hexenyl group, and a cyclohexenyl group. Examples of the oxoalkyl group can include, but are not limited to the following, a 2-oxocyclopentyl group, a 2-oxocyclohexyl group, a 2-oxopropyl group, a 2-cyclopentyl-2-oxoethyl group, a 2-cyclohexyl-2-oxoethyl group, and a 2-(4-methylcyclohexyl)-2-oxoethyl group. Examples of the oxoalkenyl group include, but are not limited to the following, a 2-oxo-4-cyclohexenyl group and a 2-oxo-4-propenyl group. Examples of the aryl group include, but are not limited to the following, a phenyl group, a naphthyl group, alkoxyphenyl groups such as a p-methoxyphenyl group, a m-methoxyphenyl group, an o-methoxyphenyl group, an ethoxyphenyl group, a p-tert-butoxyphenyl group, and a m-tert-butoxyphenyl group; alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group; alkylnaphthyl groups such as a methylnaphthyl group and an ethylnaphthyl group; alkoxynaphthyl groups such as a methoxynaphthyl group and an ethoxynaphthyl group; dialkylnaphthyl groups such as a dimethylnaphthyl group and a diethylnaphthyl group; and dialkoxynaphthyl groups such as a dimethoxynaphthyl group and a diethoxynaphthyl group. Examples of the aralkyl group include, but are not limited to the following, a benzyl group, a phenylethyl group, and a phenethyl group. Examples of the aryloxoalkyl group include, but are not limited to the following, 2-aryl-2-oxoethyl groups such as a 2-phenyl-2-oxoethyl group, a 2-(1-naphthyl)-2-oxoethyl group, and a 2-(2-naphthyl)-2-oxoethyl group. Examples of the non-nucleophilic counter ion, K$^-$, include, but are not limited to the following, halide ions such as a chloride ion and a bromide ion; fluoroalkyl sulfonates such as triflate, 1,1,1-trifluoroethane sulfonate, and nonafluorobutane sulfonate; aryl sulfonates such as tosylate, benzene sulfonate, 4-fluorobenzene sulfonate, and 1,2,3,4,5-pentafluorobenzene sulfonate; and alkyl sulfonates such as mesylate and butane sulfonate.

In the case where $R^{101d}$, $R^{101e}$, $R^{101f}$ and $R^{101g}$ are each a heteroaromatic ring having the nitrogen atom(s) in the formula, examples of the heteroaromatic ring include imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline and 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivative, and uridine derivatives.

The onium salts of the formula (P1a-1) and the formula (P1a-2) have functions as a photo acid generating agent and a thermal acid generating agent. The onium salt of the formula (P1a-3) has a function as a thermal acid generating agent.

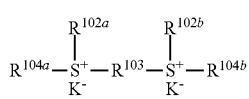

(P1b)

In the formula (P1b), each of $R^{102a}$ and $R^{102b}$ independently represents a linear, branched or cyclic alkyl group having 1 to 8 carbon atoms. $R^{103}$ represents a linear, branched or cyclic alkylene group having 1 to 10 carbon atoms. Each of $R^{104a}$ and $R^{104b}$ independently represents a 2-oxoalkyl group having 3 to 7 carbon atoms. K$^-$ represents a non-nucleophilic counter ion.

Specific examples of $R^{102a}$ and $R^{102b}$ include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cyclopropylmethyl group, a 4-methyl cyclohexyl group, and a cyclohexylmethyl group. Specific examples of $R^{103}$ include, but are not limited to the following, a methylene group, an ethylene group, a propylene group, a butylene group, a pentylene group, a hexylene group, a heptylene group, an octylene group, a nonylene group, a 1,4-cyclohexylene group, a 1,2-cyclohexylene group, a 1,3-cyclopentylene group, a 1,4-cyclooctylene group, and a 1,4-cyclohexanedimethylene group. Specific examples of $R^{104a}$ and $R^{104b}$ include, but are not limited to the following, a 2-oxopropyl group, a 2-oxocyclopentyl group, a 2-oxocyclohexyl group, and a 2-oxocycloheptyl group. K$^-$ includes the same as those described in the formula (P1a-1), (P1a-2) and (P1a-3).

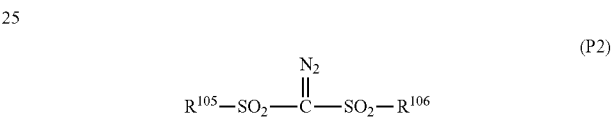

In the formula (P2), each of $R^{105}$ and $R^{106}$ independently represents a linear, branched or cyclic alkyl group or halogenated alkyl group having 1 to 12 carbon atoms, an aryl group or halogenated aryl group having 6 to 20 carbon atoms, or an aralkyl group having 7 to 12 carbon atoms.

Examples of the alkyl group in each of $R^{105}$ and $R^{106}$ include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, an amyl group, a cyclopentyl group, a cyclohexyl group, a cycloheptyl group, a norbornyl group, and an adamantyl group. Examples of the halogenated alkyl group include, but are not limited to the following, a trifluoromethyl group, a 1,1,1-trifluoroethyl group, a 1,1,1-trichloroethyl group, and a nonafluorobutyl group. Examples of the aryl group include, but are not limited to the following, alkoxyphenyl groups such as a phenyl group, a p-methoxyphenyl group, a m-methoxyphenyl group, an o-methoxyphenyl group, an ethoxyphenyl group, a p-tert-butoxyphenyl group, and a m-tert-butoxyphenyl group; and alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group. Examples of the halogenated aryl group include, but are not limited to the following, a fluorophenyl group, a chlorophenyl group, and a 1,2,3,4,5-pentafluorophenyl group. Examples of the aralkyl group include, but are not limited to the following, a benzyl group and a phenethyl group.

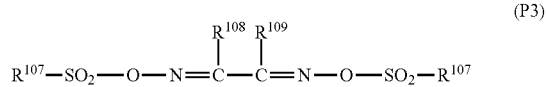

(P3)

In the formula (P3), each of $R^{107}$, $R^{108}$ and $R^{109}$ independently represents a linear, branched or cyclic alkyl group or halogenated alkyl group having 1 to 12 carbon atoms; an aryl group or halogenated aryl group having 6 to 20 carbon atoms; or an aralkyl group having 7 to 12 carbon atoms. $R^{108}$ and $R^{109}$ may be bonded with each other to form a cyclic structure, and if forming a cyclic structure, each of $R^{108}$ and $R^{109}$ represents a linear or branched alkylene group having 1 to 6 carbon atoms.

The alkyl group, halogenated alkyl group, aryl group, halogenated aryl group, and aralkyl group in each of $R^{107}$, $R^{108}$ and $R^{109}$ include the same as those described in $R^{105}$ and $R^{106}$. Herein, examples of the alkylene group in each of $R^{108}$ and $R^{109}$ include, but are not limited to the following, a methylene group, an ethylene group, a propylene group, a butylene group, and a hexylene group.

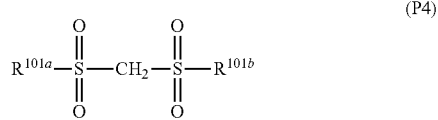
(P4)

In the formula (P4), $R^{101a}$ and $R^{101b}$ are the same as those described above.

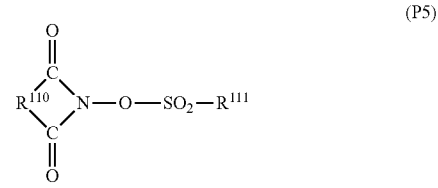
(P5)

In the formula (P5), $R^{110}$ represents an arylene group having 6 to 10 carbon atoms, an alkylene group having 1 to 6 carbon atoms, or an alkenylene group having 2 to 6 carbon atoms, and a part or all of hydrogen atoms of these groups may be further substituted with a linear or branched alkyl group or alkoxy group having 1 to 4 carbon atoms, a nitro group, an acetyl group, or a phenyl group. $R^{111}$ represents a linear, branched or substituted alkyl group, alkenyl group or alkoxyalkyl group having 1 to 8 carbon atoms, a phenyl group, or a naphthyl group, and a part or all of hydrogen atoms of these groups may be further substituted with an alkyl group or alkoxy group having 1 to 4 carbon atoms; a phenyl group that may be substituted with an alkyl group or alkoxy group having 1 to 4 carbon atoms, a nitro group, or an acetyl group; a heteroaromatic group having 3 to 5 carbon atoms; or a chlorine atom or a fluorine atom.

Herein, examples of the arylene group in $R^{110}$ include, but are not limited to the following, a 1,2-phenylene group and a 1,8-naphthylene group. Examples of the alkylene group include, but are not limited to the following, a methylene group, an ethylene group, a trimethylene group, a tetramethylene group, a phenylethylene group, and a norbornane-2,3-diyl group. Examples of the alkenylene group include, but are not limited to the following, a 1,2-vinylene group, a 1-phenyl-1,2-vinylene group, and a 5-norbornene-2,3-diyl group. The alkyl group in $R^{111}$ includes the same as those in $R^{101a}$ to $R^{101c}$. Examples of the alkenyl group include, but are not limited to the following, a vinyl group, a 1-propenyl group, an allyl group, a 1-butenyl group, a 3-butenyl group, an isoprenyl group, a 1-pentenyl group, a 3-pentenyl group, a 4-pentenyl group, a dimethylallyl group, a 1-hexenyl group, a 3-hexenyl group, a 5-hexenyl group, a 1-heptenyl group, a 3-heptenyl group, a 6-heptenyl group, and a 7-octenyl group. Examples of the alkoxyalkyl group include, but are not limited to the following, a methoxymethyl group, an ethoxymethyl group, a propoxymethyl group, a butoxymethyl group, a pentyloxymethyl group, a hexyloxymethyl group, a heptyloxymethyl group, a methoxyethyl group, an ethoxyethyl group, a propoxyethyl group, a butoxyethyl group, a pentyloxyethyl group, a hexyloxyethyl group, a methoxypropyl group, an ethoxypropyl group, a propoxypropyl group, a butoxypropyl group, a methoxybutyl group, an ethoxybutyl group, a propoxybutyl group, a methoxypentyl group, an ethoxypentyl group, a methoxyhexyl group, and a methoxyheptyl group.

Herein, Examples of the alkyl group having 1 to 4 carbon atoms, which may be further substituted, include, but are not limited to the following, a methyl group, an ethyl group, a propyl group, an isopropyl group, a n-butyl group, a an isobutyl group, and a tert-butyl group. Examples of the alkoxy group having 1 to 4 carbon atoms include, but are not limited to the following, a methoxy group, an ethoxy group, a propoxy group, an isopropoxy group, a n-butoxy group, an isobutoxy group, and tert-butoxy group. Examples of the phenyl group that may be substituted with an alkyl group or alkoxy group having 1 to 4 carbon atoms, a nitro group, or an acetyl group include, but are not limited to the following, a phenyl group, a tolyl group, a p-tert-butoxyphenyl group, a p-acetylphenyl group, and a p-nitrophenyl group. Examples of the heteroaromatic group having 3 to 5 carbon atoms include, but are not limited to the following, a pyridyl group and a furyl group.

Specific examples of the acid generating agent include, but are not limited to the following, onium salts such as tetramethylammonium trifluoromethanesulfonate, tetramethylammonium nonafluorobutanesulfonate, triethylammonium nonafluorobutanesulfonate, pyridinium nonafluorobutanesulfonate, triethylammonium camphorsulfonate, pyridinium camphorsulfonate, tetra n-butylammonium nonafluorobutanesulfonate, tetraphenylammonium nonafluorobutanesulfonate, tetramethylammonium p-toluenesulfonate, diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris (p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl) sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylene bis [methyl(2-oxocyclopentyl)sulfonium trifluoromethanesulfonate], and 1,2'-naphthylcarbonylmethyltetrahydrothiophenium triflate;

diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane; glyoxime derivatives such as bis-(p-toluenesulfonyl)-α-dimethylglyoxime, bis-(p-toluesulfonyl)-α-diphenylglyoxime, bis-(p-toluenesulfonyl)-α-dicyclohexylglyoxime, bis-(p-toluenesulfonyl)-2,3-pentanedioneglyoxime, bis-(p-toluenesulfonyl)-2-methyl-3,4-pentanedioneglyoxime, bis-(n-butanesulfonyl)-α-dimethylglyoxime, bis-(n-butanesulfonyl)-α-diphenylglyoxime, bis-(n-butanesulfonyl)-α-dicyclohexylglyoxime, bis-(n-butanesulfonyl)-2,3-pentanedioneglyoxime, bis-(n-butanesulfonyl)-2-methyl-3,4-pentanedioneglyoxime, bis-(methanesulfonyl)-α-dimethylglyoxime, bis-(trifluoromethanesulfonyl)-α-dimethylglyoxime, bis-(1,1,1-trifluoroethanesulfonyl)-α-dimethylglyoxime, bis-(tert-butanesulfonyl)-α-dimethylglyoxime, bis-(perfluorooctanesulfonyl)-α-dimethylglyoxime, bis-(cyclohexanesulfonyl)-α-dimethylglyoxime, bis-(benzenesulfonyl)-α-dimethylglyoxime, bis-(p-fluorobenzenesulfonyl)-α-dimethylglyoxime, bis-(p-tert-butylbenzenesulfonyl)-α-dimethylglyoxime, bis-(xylenesulfonyl)-α-dimethylglyoxime, and bis-(camphorsulfonyl)-α-dimethylglyoxime; bissulfone derivatives, such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane; β-ketosulfone derivatives such as 2-cyclohexylcarbonyl-2-(p-toluenesulfonyl)propane and 2-isopropylcarbonyl-2-(p-toluenesulfonyl)propane; disulfone derivatives such as a diphenyldisulfone derivative and a dicyclohexyldisulfone derivative, nitrobenzylsulfonate derivatives such as 2,6-dinitrobenzyl p-toluenesulfonate and 2,4-dinitrobenzyl p-toluenesulfonate; sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and sulfonic acid ester derivatives of a N-hydroxyimide compound, such as N-hydroxysuccinimide methanesulfonic acid ester, N-hydroxysuccinimide trifluoromethanesulfonic acid ester, N-hydroxysuccinimide ethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide 1-octanesulfonic acid ester, N-hydroxysuccinimide p-toluenesulfonic acid ester, N-hydroxysuccinimide p-methoxybenzenesulfonic acid ester, N-hydroxysuccinimide 2-chloroethanesulfonic acid ester, N-hydroxysuccinimide benzenesulfonic acid ester, N-hydroxysuccinimide-2,4,6-trimethylbenzenesulfonic acid ester, N-hydroxysuccinimide 1-naphthalenesulfonic acid ester, N-hydroxysuccinimide 2-naphthalenesulfonic acid ester, N-hydroxy-2-phenylsuccinimide methanesulfonic acid ester, N-hydroxymaleimide methanesulfonic acid ester, N-hydroxymaleimide ethanesulfonic acid ester, N-hydroxy-2-phenylmaleimide methanesulfonic acid ester, N-hydroxyglutarimide methanesulfonic acid ester, N-hydroxyglutarimide benzenesulfonic acid ester, N-hydroxyphthalimide methanesulfonic acid ester, N-hydroxyphthalimide benzenesulfonic acid ester, N-hydroxyphthalimide trifluoromethanesulfonic acid ester, N-hydroxyphthalimide p-toluenesulfonic acid ester, N-hydroxynaphthalimide methanesulfonic acid ester, N-hydroxynaphthalimide benzenesulfonic acid ester, N-hydroxy-5-norbornene-2,3-dicarboxyimide methanesulfonic acid ester, N-hydroxy-5-norbornene-2,3-dicarboxyimide trifluoromethanesulfonic acid ester, and N-hydroxy-5-norbornene-2,3-dicarboxyimide p-toluenesulfonic acid ester.

Among them, in particular, onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, and 1,2'-naphthylcarbonylmethyltetrahydrothiophenium triflate; diazomethane derivatives such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis(tert-butylsulfonyl)diazomethane; glyoxime derivatives such as bis-(p-toluenesulfonyl)-α-dimethylglyoxime and bis-(n-butanesulfonyl)-α-dimethylglyoxime, bissulfone derivatives such as bisnaphthylsulfonylmethane; and sulfonic acid ester derivatives of an N-hydroxyimide compound, such as N-hydroxysuccinimide methanesulfonic acid ester, N-hydroxysuccinimide trifluoromethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide p-toluenesulfonic acid ester, N-hydroxynaphthalimide methanesulfonic acid ester, and N-hydroxynaphthalimide benzenesulfonic acid ester, and the like are preferably used.

In the composition for forming an underlayer film for lithography according to the present embodiment, the content of the acid generating agent is not particularly limited, but the content is preferably 0.1 to 50 parts by mass and more preferably 0.5 to 40 parts by mass, based on 100 parts by mass of the material for forming an underlayer film for lithography. The content is set within the above range to result in a tendency to increase the acid generation amount to promote a crosslinking reaction, and also to result in a tendency to suppress the occurrence of the mixing phenomenon with a resist layer.

[Basic Compound]

Furthermore, the composition for forming an underlayer film for lithography of the present embodiment may contain a basic compound from the viewpoint of improving preservation stability.

The basic compound serves as a quencher to an acid for preventing a trace amount of the acid generated from the acid generating agent from promoting a crosslinking reaction. Examples of such a basic compound include primary, secondary, and tertiary aliphatic amines, mixed amines, aromatic amines, heterocyclic amines, a nitrogen-containing compound having a carboxy group, a nitrogen-containing compound having a sulfonyl group, a nitrogen-containing compound having a hydroxyl group, a nitrogen-containing compound having a hydroxyphenyl group, an alcoholic nitrogen-containing compound, an amide derivative, and an imide derivative, but are not limited thereto.

Specifically, specific examples of the primary aliphatic amines include, but are not limited to the following, ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Specific examples of the secondary aliphatic amines include, but are not limited to the following, dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Specific examples of the tertiary aliphatic amines include, but are not limited to the following, trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Specific examples of the mixed amines include, but are not limited to the following, dimethylethylamine, methylethylpropylamine, benzylamine, phenethylamine, and benzyldimethylamine. Specific examples of the aromatic amines and heterocyclic amines include, but are not limited to the following, aniline derivatives (for example, aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (for example, pyrrole, 2H-pyrrole, 1-methylpyrrole, 2,4-dimethylpyrrole, 2,5-dimethylpyrrole, and N-methylpyrrole), oxazole derivatives (for example, oxazole and isoxazole), thiazole derivatives (for example, thiazole and isothiazole), imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline, 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Furthermore, specific examples of the nitrogen-containing compound having a carboxy group include, but are not limited to the following, aminobenzoic acid, indolecarboxylic acid, and amino acid derivatives (for example, nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Specific examples of the nitrogen-containing compound having a sulfonyl group include, but are not limited to the following, 3-pyridinesulfonic acid and pyridinium p-toluenesulfonate. Specific examples of the nitrogen-containing compound having a hydroxyl group, the nitrogen-containing compound having a hydroxyphenyl group, and the alcoholic nitrogen-containing compound include, but are not limited to the following, 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Specific examples of the amide derivative include, but are not limited to the following, formamide, N-methylformamide, N,N-dimethylformamide, acetamide, N-methylacetamide, N,N-dimethylacetamide, propionamide, and benzamide. Specific examples of the imide derivative include, but are not limited to the following, phthalimide, succinimide, and maleimide.

In the composition for forming an underlayer film for lithography according to the present embodiment, the content of the basic compound is not particularly limited, but the content is preferably 0.001 to 2 parts by mass and more preferably 0.01 to 1 part by mass, based on 100 parts by mass of the material for forming an underlayer film for lithography. The content is set within the above preferable range to result in a tendency to improve preservation stability without excessively interrupting a crosslinking reaction.

In addition, the composition for forming an underlayer film for lithography of the present embodiment may contain other resins and/or compounds for the purpose of imparting heat curability and controlling absorbance. Such other resins and/or compounds include naphthol resins, xylene resins, naphthol-modified resins, phenol-modified resins of naphthalene resins, polyhydroxystyrene, dicyclopentadiene resins, (meth)acrylate, dimethacrylate, trimethacrylate, tetramethacrylate, resins having a naphthalene ring such as vinylnaphthalene and polyacenaphthylene, resins having a biphenyl ring such as phenanthrenequinone and fluorene, resins having a heterocyclic ring having a hetero atom such as thiophene and indene, and resins not containing an aromatic ring; rosin-based resins, and resins or compounds including an alicyclic structure, such as cyclodextrin, adamantane(poly)ol, tricyclodecane(poly)ol and derivatives thereof, but are not limited thereto. Furthermore, the composition for forming an underlayer film for lithography of the present embodiment can also contain a known additive. Examples of the known additive includes, but not limited to the following, an ultraviolet absorber, a surfactant, a colorant and a non-ionic surfactant.

[Underlayer Film for Lithography and Multilayer Resist Pattern Forming Method]

An underlayer film for lithography of the present embodiment is formed from the composition for forming an underlayer film for lithography of the present embodiment.

In addition, a resist pattern forming method of the present embodiment includes step (A-1) of forming an underlayer film on a substrate by using the composition for forming an underlayer film for lithography of the present embodiment, step (A-2) of forming at least one photoresist layer on the underlayer film, and step (A-3) of, after the second forming step, irradiating a predetermined region of the photoresist layer with radiation, followed by developing.

Furthermore, a circuit pattern forming method of the present embodiment includes step (B-1) of forming an underlayer film on a substrate by using the composition for forming an underlayer film for lithography of the present embodiment, step (B-2) of forming an intermediate layer film on the underlayer film by using a silicon atom-containing resist intermediate layer film material, step (B-3) of forming at least one photoresist layer on the intermediate layer film, step (B-4) of, after step (B-3), irradiating a predetermined region of the photoresist layer with radiation, followed by developing to form a resist pattern, and step (B-5) of, after step (B-4), etching the intermediate layer film with the resist pattern as a mask, etching the underlayer film with the obtained intermediate layer film pattern as an etching mask and etching the substrate with the obtained underlayer film pattern as an etching mask, to form a pattern on the substrate.

The underlayer film for lithography of the present embodiment is not particularly limited in terms of the forming method thereof as long as it is formed from the composition for forming an underlayer film for lithography of the present embodiment, and a known method can be applied. For example, the underlayer film can be formed by applying the composition for forming an underlayer film for lithography of the present embodiment on the substrate by a known coating method or printing method such as spin coating or screen printing, and removing an organic solvent by volatilization or the like.

The underlayer film is preferably baked upon forming in order to suppress the occurrence of the mixing phenomenon with an upperlayer resist and also promote a crosslinking reaction. In this case, the baking temperature is not particularly limited, but it is preferably within the range of 80 to 450° C., and more preferably 200 to 400° C. In addition, the baking time is not also particularly limited, but is preferably within the range of 10 to 300 seconds. Herein, the thickness of the underlayer film can be appropriately selected depending on the required properties, and is not particularly limited, but the thickness is usually preferably about 30 to 20,000 nm and more preferably 50 to 15,000 nm.

After the underlayer film is prepared, in the case of a two-layer process, a silicon-containing resist layer or a usual single-layer resist including a hydrocarbon is preferably prepared on the underlayer film, and in the case of a three-layer process, a silicon-containing intermediate layer is preferably prepared on the underlayer film, and a single-layer resist layer not containing silicon is preferably prepared on the silicon-containing intermediate layer. In these cases, known photoresist materials for forming the resist layer can be used.

After the underlayer film is prepared on the substrate, in the case of a two-layer process, a silicon-containing resist layer or a usual single-layer resist including a hydrocarbon can be prepared on the underlayer film. In the case of a three-layer process, a silicon-containing intermediate layer can be prepared on the underlayer film, and a single-layer resist layer not containing silicon can be prepared on the silicon-containing intermediate layer. In these cases, a photoresist material for forming the resist layer, which can be used, is appropriately selected from known ones, and is not particularly limited.

As the silicon-containing resist material for a two-layer process, a positive-type photoresist material, which contains a silicon atom-containing polymer such as a polysilsesquioxane derivative or a vinylsilane derivative, is preferably used as a base polymer from the viewpoint of oxygen gas-etching resistance. Also, an organic solvent, an acid generating agent and if necessary a basic compound can preferably used. Herein, as the silicon atom-containing polymer, a known polymer used in such a resist material can be used.

As the silicon-containing intermediate layer for a three-layer process, a polysilsesquioxane-based intermediate layer is preferably used. The intermediate layer is allowed to have an effect as an antireflective film, and thus tends to make it possible to effectively suppress reflection. For example, if a material including many aromatic groups and having a high substrate-etching resistance is used for the underlayer film in a 193 nm exposure process, a k-value tends to be increased to increase substrate reflection, but the reflection can be suppressed by the intermediate layer to thereby make the substrate reflection 0.5% or less. For the intermediate layer having such an antireflection effect, but not limited to the following, polysilsesquioxane into which a phenyl group or a light-absorbing group having a silicon-silicon bond for 193 nm exposure is introduced and which is to be crosslinked with an acid or heat is preferably used.

An intermediate layer formed by the Chemical Vapour Deposition (CVD) method can also be used. As the intermediate layer having a high effect as an antireflective film, prepared by the CVD method, but not limited to the following, for example, a SiON film is known. In general, the intermediate layer is formed by a wet process such as a spin coating method or screen printing rather than the CVD method in terms of simplicity and cost effectiveness. Herein, the upperlayer resist in a three-layer process may be of positive-type or negative-type, and the same one as a commonly used single-layer resist can be used therefor.

Furthermore, the underlayer film of the present embodiment can also be used as a usual antireflective film for use in a single-layer resist or a usual underlying material for suppressing pattern collapse. The underlayer film of the present embodiment can also be expected to serve as a hard mask for underlying processing because of being excellent in etching resistance for underlying processing.

In the case where a resist layer is formed by the photoresist material, a wet process such as a spin coating method or screen printing is preferably used as in the case of forming the underlayer film. The resist material is coated by a spin coating method or the like and then usually pre-baked, and such pre-baking is preferably performed in the range of 80 to 180° C. for 10 to 300 seconds. Thereafter, in accordance with an ordinary method, the resultant can be subjected to exposure, post-exposure bake (PEB), and development to obtain a resist pattern. Herein, the thickness of the resist film is not particularly limited, but generally, it is preferably 30 to 500 nm and more preferably 50 to 400 nm.

Light for use in exposure may be appropriately selected depending on the photoresist material to be used. In general, examples thereof include high energy radiation having a wavelength of 300 nm or less, specifically, excimer lasers of 248 nm, 193 nm, and 157 nm, a soft X-ray of 3 to 20 nm, electron beam, and an X-ray.

The resist pattern formed by the above method is a pattern whose collapse is suppressed by the underlayer film of the present embodiment. Therefore, the underlayer film of the present embodiment can be used to thereby obtain a finer pattern, and an exposure amount necessary for obtaining such a resist pattern can be reduced.

Then, the obtained resist pattern is used as a mask to perform etching. As the etching of the underlayer film in a two-layer process, gas etching is preferably used. As the gas etching, etching using oxygen gas is suitable. In addition to oxygen gas, an inert gas such as He and Ar, and CO, $CO_2$, $NH_3$, $SO_2$, $N_2$, $NO_2$, and $H_2$ gases can also be added. The gas etching can also be performed not using oxygen gas but using only CO, $CO_2$, $NH_3$, $N_2$, $NO_2$, and $H_2$ gases. In particular, the latter gases are preferably used for protecting a side wall for preventing a pattern side wall from being undercut.

On the other hand, also in the etching of the intermediate layer in a three-layer process, gas etching is preferably used. As the gas etching, the same one as the one described in a two-layer process can be applied. In particular, the intermediate layer is preferably processed in a three-layer process using a fluorocarbon gas with the resist pattern as a mask. Thereafter, as described above, the intermediate layer pattern is used as a mask to perform, for example, oxygen gas etching, thereby processing the underlayer film.

Herein, in the case where an inorganic hard mask intermediate layer film is formed as the intermediate layer, a silicon oxide film, a silicon nitride film, and a silicon oxynitride film (SiON film) are formed by the CVD method, the ALD method, and the like. The nitride film forming method that can be used is, but not limited to the following, any method described in, for example, Japanese Patent Laid-Open No. 2002-334869 (Patent Literature 6) and WO2004/066377 (Patent Literature 7). While the photoresist film can be directly formed on such an intermediate layer film, an organic antireflective film (BARC) may also be formed on the intermediate layer film by spin coating, and the photoresist film may also be formed thereon.

As the intermediate layer, a polysilsesquioxane-based intermediate layer is also preferably used. The resist intermediate layer film is allowed to have an effect as an antireflective film, and thus tends to make it possible to effectively suppress reflection. A specific material for the polysilsesquioxane-based intermediate layer that can be used is, but not limited to the following, any material described in, for example, Japanese Patent Laid-Open No. 2007-226170 (Patent Literature 8) and Japanese Patent Laid-Open No. 2007-226204 (Patent Literature 9).

The next etching of the substrate can also be performed by an ordinary method, and, for example, when the substrate is made of $SiO_2$ or SiN, etching with mainly a fluorocarbon gas can be performed, and when the substrate is made of p-Si, Al, or W, etching mainly using a chlorine-based gas or bromine-based gas can be performed. In the case where the substrate is processed by the etching with a fluorocarbon gas, the silicon-containing resist in a two-layer resist process and the silicon-containing intermediate layer in a three-layer process are peeled off at the same time as the processing of the substrate. On the other hand, in the case where the substrate is processed by the etching with a chlorine-based gas or bromine-based gas, the silicon-containing resist layer or the silicon-containing intermediate layer is peeled off separately, and is generally peeled off by dry etching with a fluorocarbon gas after the substrate is processed.

The underlayer film of the present embodiment is characterized by being excellent in etching resistance of such a substrate. Herein, the substrate that can be used is appropriately selected from known ones, and is not particularly limited, but includes Si, α-Si, p-Si, $SiO_2$, SiN, SiON, W, TiN, and Al substrates. In addition, the substrate may also be a laminate having a processed film (processed substrate) on a base material (support). Such a processed film includes various Low-k films made of Si, $SiO_2$, SiON, SiN, p-Si, α-Si, W, W—Si, Al, Cu, and Al—Si, and stopper films thereof, and a material different from the base material (support) is usually used therefor. Herein, the thickness of the substrate to be processed or the processed film is not particularly limited, but it is usually preferably about 50 to 10,000 nm and more preferably 75 to 5,000 nm.

[Method for Purifying Compound or Resin]

A method for purifying the compound or the resin of the present embodiment includes a step of bringing a solution including an organic solvent optionally immiscible with water and the compound or the resin into contact with an acidic aqueous solution for extraction. More specifically, in the present embodiment, the compound represented by the formula (1) or the resin obtained by using the compound as a monomer can be purified by dissolving the compound or the resin in an organic solvent optionally immiscible with water, bringing the solution into contact with an acidic aqueous solution for performing an extraction treatment, to thereby transfer a metal content included in the solution (A) including the compound or the resin and the organic solvent to an aqueous phase, and then separating an organic phase and the aqueous phase. The purification method of the present embodiment can allow the contents of various metals in the compound represented by the formula (1) or the resin obtained by using the compound as a monomer to be remarkably reduced.

In the present embodiment, the organic solvent optionally immiscible with water means an organic solvent whose solubility in water at room temperature is less than 30%. Herein, the solubility is preferably less than 20%, more preferably less than 10%. The organic solvent optionally immiscible with water is not particularly limited, but it is preferably an organic solvent that can be safely applied to a semiconductor manufacturing process. The amount of the organic solvent to be used is usually about 1 to 100 times the amount of the compound represented by the formula (1) or the resin obtained by using the compound as a monomer, to be used.

Specific examples of the solvent to be used include, but not limited to the following, ethers such as diethyl ether and diisopropyl ether, esters such as ethyl acetate, butyl acetate and isoamyl acetate, ketones such as methyl ethyl ketone, 1,2-diethoxyketone, methyl isobutyl ketone, ethyl isobutyl ketone, cyclohexanone, cyclopentanone, 2-heptanone and 2-pentanone, glycol ether acetates such as ethylene glycol monoethyl ether acetate, ethylene glycol monobutyl ether acetate, propylene glycol monomethyl ether acetate (PG- MEA) and propylene glycol monoethyl ether acetate, aliphatic hydrocarbons such as n-hexane and n-heptane, aromatic hydrocarbons such as toluene and xylene, and halogenated hydrocarbons such as methylene chloride and chloroform. Among them, toluene, 2-heptanone, cyclohexanone, cyclopentanone, methyl isobutyl ketone, propylene glycol monomethyl ether acetate, 1,2-diethoxyketone, butyl acetate, ethyl acetate, and the like are preferable, and cyclohexanone and propylene glycol monomethyl ether acetate are more preferable. These solvents can be used singly or as a mixture of two or more thereof.

The acidic aqueous solution to be used in the present embodiment is appropriately selected from aqueous solutions in which an organic or inorganic compound commonly known is dissolved in water. Examples include an aqueous solution in which a mineral acid such as hydrochloric acid, sulfuric acid, nitric acid or phosphoric acid is dissolved in water, or an aqueous solution in which an organic acid such as acetic acid, propionic acid, oxalic acid, malonic acid, succinic acid, fumaric acid, maleic acid, tartaric acid, citric acid, methanesulfonic acid, phenolsulfonic acid, p-toluenesulfonic acid or trifluoroacetic acid is dissolved in water. These acidic aqueous solutions can be used singly or in combinations of two or more thereof. Among these acidic aqueous solutions, an aqueous solution of sulfuric acid, nitric acid, or a carboxylic acid such as acetic acid, oxalic acid, tartaric acid or citric acid is preferable, an aqueous solution of sulfuric acid, oxalic acid, tartaric acid or citric acid is more preferable, and an aqueous solution of oxalic acid is further preferable. It is considered that a polyvalent carboxylic acid such as oxalic acid, tartaric acid and citric acid is coordinated with a metal ion to exert a chelating effect, and therefore tends to allow a metal to be more effectively removed. In addition, the water to be here used is preferably water having a low metal content according to the purpose of the present embodiment, such as ion-exchange water.

The pH of the acidic aqueous solution to be used in the present embodiment is not particularly limited, but the acidity of the aqueous solution is preferably adjusted in consideration of the effect on the compound represented by the formula (1) or the resin obtained by using the compound as a monomer. The pH is usually in the range from about 0 to 5, more preferably about 0 to 3.

The amount of the acidic aqueous solution to be used in the present embodiment is not particularly limited, but the amount to be used is preferably adjusted from the viewpoint of reducing the number of extractions for metal removal and the viewpoint of ensuring operation property in consideration of the total amount of the liquid. The amount of the aqueous solution to be used is usually 10 to 200% by mass, preferably 20 to 100% by mass, relative to the solution of the compound represented by the formula (1) or the resin obtained by using the compound as a monomer, dissolved in the organic solvent.

In the present embodiment, the acidic aqueous solution is brought into contact with the solution (A) including the compound represented by the formula (1) or the resin obtained by using the compound as a monomer and the organic solvent optionally immiscible with water, to thereby extract the metal content.

The temperature in performing of the extraction treatment is usually in the range from 20 to 90° C., preferably 30 to 80° C. The extraction operation is performed by, for example, well mixing with stirring or the like and thereafter standing. Thus, the metal content included in the solution including the compound represented by the formula (1) or the resin obtained by using the compound as a monomer and the organic solvent is transferred to the aqueous phase. In addition, the operation can allow the acidity of the solution to be reduced, suppressing the change of properties of the compound represented by the formula (1) or the resin obtained by using the compound as a monomer.

The resulting mixture is separated to the solution phase including the compound represented by the formula (1) or the resin obtained by using the compound as a monomer and the organic solvent, and the aqueous phase, and therefore the solution including the compound represented by the formula (1) or the resin obtained by using the compound as a monomer and the organic solvent is recovered by decantation or the like. The standing time is not particularly limited, but the standing time is preferably adjusted from the viewpoint of providing better separation to the solution phase including the organic solvent, and the aqueous phase. The standing time is usually 1 minute or more, preferably 10 minutes or more, more preferably 30 minutes or more. In addition, the extraction treatment may be performed only once, but is also effectively performed with operations such as mixing, standing and separation being repeatedly performed multiple times.

In the present embodiment, a step of performing an extraction treatment with water is preferably further included after the step of bringing the solution (A) into contact with the acidic aqueous solution for extraction. That is, preferably, the extraction treatment is performed by using the acidic aqueous solution, thereafter the solution (A) including the compound represented by the formula (1) or the resin obtained by using the compound as a monomer, extracted and recovered from the aqueous solution, and the organic solvent, is preferably further subjected to the extraction treatment with water. The extraction operation with water is performed by, for example, well mixing with stirring or the like and thereafter standing. The resulting solution is separated to the solution phase including the compound represented by the formula (1) or the resin obtained by using the compound as a monomer and the organic solvent, and the aqueous phase, and therefore the solution phase including the compound represented by the formula (1) or the resin obtained by using the compound as a monomer and the organic solvent is recovered by decantation or the like. In addition, the water to be here used is preferably water having a low metal content according to the purpose of the present embodiment, such as ion-exchange water. The extraction treatment may be performed only once, but is also effectively performed with operations such as mixing, standing and separation being repeatedly performed multiple times. In addition, conditions in the extraction treatment, such as the ratio of both to be used, the temperature and the time, are not particularly limited, but may be the same as in the case of the contact treatment with the acidic aqueous solution above.

The water content that can be incorporated in the solution thus obtained, including the compound represented by the formula (1) or the resin obtained by using the compound as a monomer and the organic solvent, can be easily removed by performing an operation such as distillation under reduced pressure. In addition, an organic solvent can be if necessary added to adjust the concentration of the compound represented by the formula (1) or the resin obtained by using the compound as a monomer to any concentration.

The method of isolating the compound represented by the formula (1) or the resin obtained by using the compound as a monomer from the resulting solution including the compound represented by the formula (1) or the resin obtained by using the compound as a monomer and the organic solvent can be performed by a known method such as removal under reduced pressure, separation by reprecipitation and a combination thereof. If necessary, a known treatment such as a concentration operation, a filtration operation, a centrifugation operation and a drying operation can be performed.

EXAMPLES

Hereinafter, the present embodiment will be described by Examples and Comparative Examples in more detail, but the present embodiment is not limited thereto at all.

(Carbon Concentration and Oxygen Concentration)

The carbon concentration and the oxygen concentration (% by mass) were measured by organic element analysis.

Apparatus: CHN CORDER MT-6 (manufactured by Yanaco Bunseki Kogyo Co.)

(Molecular Weight)

Measurement was performed by LC-MS analysis using Acquity UPLC/MALDI-Synapt HDMS manufactured by Water.

(Molecular Weight in Terms of Polystyrene)

Gel permeation chromatography (GPC) analysis was used to determine the weight average molecular weight (Mw) and the number average molecular weight (Mn) in terms of polystyrene, and to determine the degree of dispersion (Mw/Mn).

Apparatus: Shodex GPC-101 type (manufactured by Showa Denko K. K.)
Column: KF-80M×3
Eluent: THF 1 mL/min
Temperature: 40° C.

(Pyrolysis Temperature (Tg))

An EXSTAR 6000 DSC apparatus manufactured by SII NanoTechnology Inc. was used, and about 5 mg of a sample was placed in an unsealed aluminum container and heated to 500° C. at a rate of temperature rise of 10° C./min in a nitrogen gas (30 mL/min) stream. In this time, a temperature at which a reducing portion appeared on the base line was defined as a pyrolysis temperature (Tg).

(Solubility)

The amount of each compound dissolved in 1-methoxy-2-propanol (PGME) and propylene glycol monomethyl ether acetate (PGMEA) was measured at 23° C., and the results were evaluated according to the following criteria.
Evaluation A: 10% by weight or more
Evaluation B: 5% by weight or more and less than 10% by weight
Evaluation C: less than 5% by weight (Synthesis Example 1) Synthesis of CAX-1

A container having an inner volume of 200 mL, equipped with a stirrer, a condenser and a burette, was prepared. To this container were charged 17.8 g (80 mmol) of N-ethyl-carbazole-3-carbaldehyde (produced by Nisshoku Techno Fine Chemical Co., Ltd.), 25.6 g (160 mmol) of 2,6-dihydroxynaphthalene (reagent produced by Tokyo Chemical Industry Co., Ltd.) and 100 mL of 1,4-dioxane (reagent produced by Kanto Chemical Co., Inc.), and 3.9 g (21 mmol) of p-toluenesulfonic acid (reagent produced by Kanto Chemical Co., Inc.) was added thereto to prepare a reaction liquid. The reaction liquid was stirred at 90° C. for 6 hours to perform a reaction. Then, a neutralization treatment was performed by a 24% aqueous sodium hydroxide solution (reagent produced by Kanto Chemical Co., Inc.), the reaction liquid was concentrated, 50 g of n-heptane (reagent produced by Kanto Chemical Co., Inc.) was added thereto to precipitate a reaction product, and the resultant was cooled to room temperature followed by filtration for separation. A solid obtained by filtration was dried, and thereafter separated and purified by column chromatography to thereby provide 4.2 g of an objective compound (CAX-1) represented by the following formula.

Herein, the following peaks were observed by 400 MHz-$^1$H-NMR, and it was confirmed that the compound had a chemical structure of the following formula.

$^1$H-NMR: (d-DMSO, internal standard TMS)
δ (ppm) 9.9 (2H, O—H), 7.0-8.3 (17H, Ph-H), 6.2 (1H, C—H), 4.2 (2H, CH$_2$), 1.2 (3H, CH$_3$)

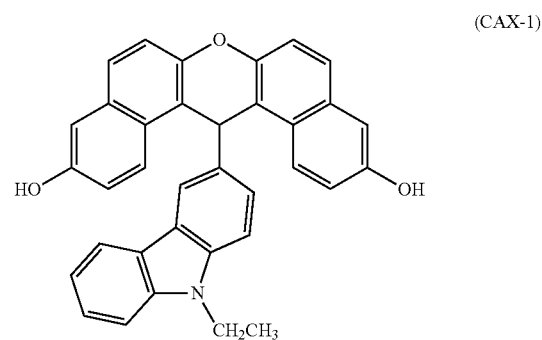 [SMILES: CCn1c2ccccc2c2cc(C3c4c(ccc5cc(O)ccc45)Oc4ccc5cc(O)ccc5c43)ccc21]

(CAX-1)

As a result of organic element analysis, the carbon concentration and the oxygen concentration of the resulting compound (CAX-1) were 82.8% and 9.4%, respectively.

The molecular weight of the resulting compound was measured by the above method, and as a result, it was 508.

As a result of thermogravimetric measurement (TG), the 10% thermal weight loss temperature of the resulting compound (CAX-1) was 400° C. or higher. Therefore, the compound was evaluated to have a high heat resistance and be applicable to high-temperature baking.

As a result of evaluation of the solubility in PGME and PGMEA, the solubility was 10% by weight or more (Evaluation A) and compound (CAX-1) was evaluated to have an excellent solubility. Therefore, compound (CAX-1) was evaluated to have a high storage stability in a solution state and also be sufficiently applicable to an edge bead rinse liquid (mixed liquid of PGME/PGMEA) widely used in a semiconductor microfabrication process.

(Synthesis Example 2) Synthesis of CAX-2

A container having an inner volume of 200 mL, equipped with a stirrer, a condenser and a burette, was prepared. To this container were charged 17.8 g (80 mmol) of N-ethyl-carbazole-3-carbaldehyde (produced by Nisshoku Techno Fine Chemical Co., Ltd.), 25.6 g (160 mmol) of 2,7-dihydroxynaphthalene (reagent produced by Tokyo Chemical Industry Co., Ltd.) and 150 mL of 1,4-dioxane (reagent produced by Kanto Chemical Co., Inc.), and 7.8 g (42 mmol) of p-toluenesulfonic acid (reagent produced by Kanto Chemical Co., Inc.) was added thereto to prepare a reaction liquid. The reaction liquid was stirred at 90° C. for 6 hours to perform a reaction. Then, a neutralization treatment was performed by a 24% aqueous sodium hydroxide solution (reagent produced by Kanto Chemical Co., Inc.), the reaction liquid was concentrated, 50 g of n-heptane (reagent produced by Kanto Chemical Co., Inc.) was added thereto to precipitate a reaction product, and the resultant was cooled to room temperature followed by filtration for separation. A solid obtained by filtration was dried, and thereafter separated and purified by column chromatography to thereby provide 3.8 g of an objective compound (CAX-2) represented by the following formula.

Herein, the following peaks were observed by 400 MHz-$^1$H-NMR, and it was confirmed that the compound had a chemical structure of the following formula.

$^1$H-NMR: (d-DMSO, internal standard TMS)
δ (ppm) 9.9 (2H, O—H), 7.0-8.1 (17H, Ph-H), 6.1 (1H, C—H), 4.4 (2H, CH$_2$), 1.3 (3H, CH$_3$)

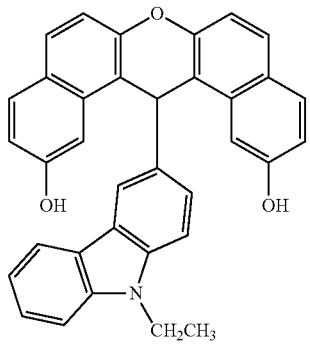

(CAX-2)

As a result of organic element analysis, the carbon concentration and the oxygen concentration of the resulting compound (CAX-2) were 82.8% and 9.4%, respectively.

The molecular weight of the resulting compound was measured by the above method, and as a result, it was 508.

As a result of thermogravimetric measurement (TG), the 10% thermal weight loss temperature of the resulting compound (CAX-2) was 400° C. or higher. The compound was evaluated to have a high heat resistance and be applicable to high-temperature baking.

As a result of evaluation of the solubility in PGME and PGMEA, the solubility was 5% by weight or more (Evaluation B) and compound (CAX-2) was evaluated to have an excellent solubility.

(Synthesis Example 3) Synthesis of CAX-3

A container having an inner volume of 200 mL, equipped with a stirrer, a condenser and a burette, was prepared. To this container were charged 17.8 g (80 mmol) of N-ethyl-carbazole-3-carbaldehyde (produced by Nisshoku Techno Fine Chemical Co., Ltd.), 29.8 g (160 mmol) of 4,4'-biphenol (reagent produced by Tokyo Chemical Industry Co., Ltd.) and 100 mL of γ-butyrolactone (reagent produced by Kanto Chemical Co., Inc.), and 7.8 g (42 mmol) of p-toluenesulfonic acid (reagent produced by Kanto Chemical Co., Inc.) was added thereto to prepare a reaction liquid. The reaction liquid was stirred at 100° C. for 8 hours to perform a reaction. Then, a neutralization treatment was performed by a 24% aqueous sodium hydroxide solution (reagent produced by Kanto Chemical Co., Inc.), the reaction liquid was concentrated, 100 g of ion-exchange water was added thereto to precipitate a reaction product, and the resultant was cooled to room temperature followed by filtration for separation. A solid obtained by filtration was dried, and thereafter separated and purified by column chromatography to thereby provide 4.8 g of an objective compound (CAX-3) represented by the following formula.

Herein, the following peaks were observed by 400 MHz-$^1$H-NMR, and it was confirmed that the compound had a chemical structure of the following formula.

$^1$H-NMR: (d-DMSO, internal standard TMS)
δ (ppm) 9.4 (4H, O—H), 6.8-7.8 (14H, Ph-H), 6.1 (1H, C—H), 4.2 (2H, CH$_2$), 1.2 (3H, CH$_3$)

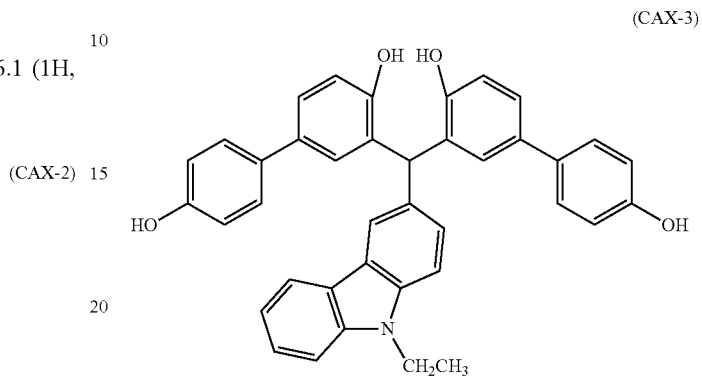

(CAX-3)

As a result of organic element analysis, the carbon concentration and the oxygen concentration of the resulting compound (CAX-3) were 81.0% and 11.0%, respectively.

The molecular weight of the resulting compound was measured by the above method, and as a result, it was 577.

As a result of thermogravimetric measurement (TG), the 10% thermal weight loss temperature of the resulting compound (CAX-3) was 400° C. or higher. The compound was evaluated to have a high heat resistance and be applicable to high-temperature baking.

As a result of evaluation of the solubility in PGME and PGMEA, the solubility was 10% by weight or more (Evaluation A) and compound (CAX-3) was evaluated to have an excellent solubility. Therefore, compound (CAX-3) was evaluated to have a high storage stability in a solution state and also be sufficiently applicable to an edge bead rinse liquid (mixed liquid of PGME/PGMEA) widely used in a semiconductor microfabrication process.

(Synthesis Example 4) Synthesis of CAX-4

A container having an inner volume of 300 mL, equipped with a stirrer, a condenser and a burette, was prepared. To this container were charged 19.8 g (80 mmol) of N-butyl-carbazole-3-carbaldehyde (produced by Nisshoku Techno Fine Chemical Co., Ltd.), 25.6 g (160 mmol) of 2,6-dihydroxynaphthalene (reagent produced by Tokyo Chemical Industry Co., Ltd.) and 100 mL of 1,4-dioxane (reagent produced by Kanto Chemical Co., Inc.), and 3.9 g (21 mmol) of p-toluenesulfonic acid (reagent produced by Kanto Chemical Co., Inc.) was added thereto to prepare a reaction liquid. The reaction liquid was stirred at 90° C. for 6 hours to perform a reaction. Then, a neutralization treatment was performed by a 24% aqueous sodium hydroxide solution (reagent produced by Kanto Chemical Co., Inc.), the reaction liquid was concentrated, 50 g of n-heptane (reagent produced by Kanto Chemical Co., Inc.) was added thereto to precipitate a reaction product, and the resultant was cooled to room temperature followed by filtration for separation. A solid obtained by filtration was dried, and thereafter separated and purified by column chromatography to thereby provide 4.2 g of an objective compound (CAX-4) represented by the following formula.

Herein, the following peaks were observed by 400 MHz-¹H-NMR, and it was confirmed that the compound had a chemical structure of the following formula.

¹H-NMR: (d-DMSO, internal standard TMS)
δ (ppm) 9.9 (2H, O—H), 7.0-8.2 (17H, Ph-H), 6.1 (1H, C—H), 3.9-4.3 (6H, CH₂), 1.2 (3H, CH₃)

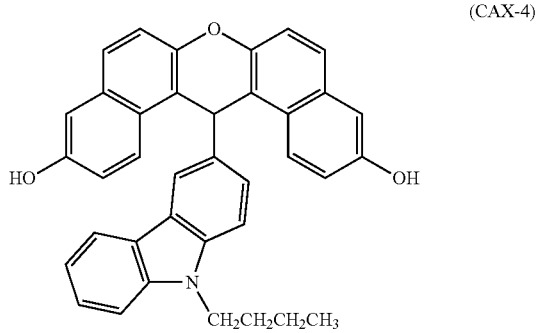

(CAX-4)

As a result of organic element analysis, the carbon concentration and the oxygen concentration of the resulting compound (CAX-4) were 82.9% and 8.9%, respectively.

The molecular weight of the resulting compound was measured by the above method, and as a result, it was 535.

As a result of thermogravimetric measurement (TG), the 10% thermal weight loss temperature of the resulting compound (CAX-4) was 400° C. or higher. The compound was evaluated to have a high heat resistance and be applicable to high-temperature baking.

As a result of evaluation of the solubility in PGME and PGMEA, the solubility was 10% by weight or more (Evaluation A) and compound (CAX-4) was evaluated to have an excellent solubility. Therefore, compound (CAX-4) was evaluated to have a high storage stability in a solution state and also be sufficiently applicable to an edge bead rinse liquid (mixed liquid of PGME/PGMEA) widely used in a semiconductor microfabrication process.

(Synthesis Example 5) Synthesis of CAX-5

A container having an inner volume of 300 mL, equipped with a stirrer, a condenser and a burette, was prepared. To this container were charged 15.6 g (80 mmol) of 9H-carbazole-1-carbaldehyde (synthesized with reference to Tetrahedron; vol. 67; nb.32; (2011); p. 5725-5731), 25.6 g (160 mmol) of 2,6-dihydroxynaphthalene (reagent produced by Tokyo Chemical Industry Co., Ltd.) and 100 mL of 1,4-dioxane (reagent produced by Kanto Chemical Co., Inc.), and 3.9 g (21 mmol) of p-toluenesulfonic acid (reagent produced by Kanto Chemical Co., Inc.) was added thereto to prepare a reaction liquid. The reaction liquid was stirred at 90° C. for 6 hours to perform a reaction. Then, a neutralization treatment was performed by a 24% aqueous sodium hydroxide solution (reagent produced by Kanto Chemical Co., Inc.), the reaction liquid was concentrated, 50 g of n-heptane (reagent produced by Kanto Chemical Co., Inc.) was added thereto to precipitate a reaction product, and the resultant was cooled to room temperature followed by filtration for separation. A solid obtained by filtration was dried, and thereafter separated and purified by column chromatography to thereby provide 2.4 g of an objective compound (CAX-5) represented by the following formula.

Herein, the following peaks were observed by 400 MHz-¹H-NMR, and it was confirmed that the compound had a chemical structure of the following formula.

¹H-NMR: (d-DMSO, internal standard TMS)
δ (ppm) 9.7-9.9 (2H, O—H), 10.9 (1H, N—H), 7.0-7.9 (16H, Ph-H), 6.0 (1H, C—H)

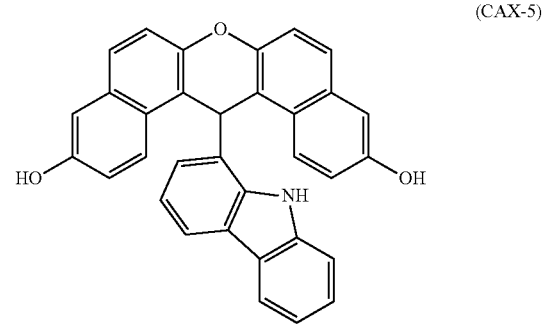 [SMILES: Oc1ccc2c3c(ccc2c1)Oc1ccc2cc(O)ccc2c1C3c1cccc2c1[nH]c1ccccc12]

(CAX-5)

As a result of organic element analysis, the carbon concentration and the oxygen concentration of the resulting compound (CAX-5) were 80.0% and 12.9%, respectively.

The molecular weight of the resulting compound was measured by the above method, and as a result, it was 495.

As a result of thermogravimetric measurement (TG), the 10% thermal weight loss temperature of the resulting compound (CAX-5) was 400° C. or higher. The compound was evaluated to have a high heat resistance and be applicable to high-temperature baking.

As a result of evaluation of the solubility in PGME and PGMEA, the solubility was 10% by weight or more (Evaluation A) and compound (CAX-5) was evaluated to have an excellent solubility. Therefore, compound (CAX-5) was evaluated to have a high storage stability in a solution state and also be sufficiently applicable to an edge bead rinse liquid (mixed liquid of PGME/PGMEA) widely used in a semiconductor microfabrication process.

(Synthesis Example 6) Synthesis of CAX-6

A container having an inner volume of 300 mL, equipped with a stirrer, a condenser and a burette, was prepared. To this container were charged 18.0 g (80 mmol) of 1-methoxy-9H-carbazole-3-carbaldehyde (murrayanine; synthesized with reference to Knolker, H.-J.; Bauermeister, M. J. Chem. Soc. Chem. Commun. 1990, 664.), 25.6 g (160 mmol) of 2,6-dihydroxynaphthalene (reagent produced by Tokyo Chemical Industry Co., Ltd.) and 100 mL of 1,4-dioxane (reagent produced by Kanto Chemical Co., Inc.), and 3.9 g (21 mmol) of p-toluenesulfonic acid (reagent produced by Kanto Chemical Co., Inc.) was added thereto to prepare a reaction liquid. The reaction liquid was stirred at 90° C. for 6 hours to perform a reaction. Then, a neutralization treatment was performed by a 24% aqueous sodium hydroxide solution (reagent produced by Kanto Chemical Co., Inc.), the reaction liquid was concentrated, 50 g of n-heptane (reagent produced by Kanto Chemical Co., Inc.) was added thereto to precipitate a reaction product, and the resultant was cooled to room temperature followed by filtration for separation. A solid obtained by filtration was dried, and thereafter separated and purified by column chromatography to thereby provide 2.4 g of an objective compound (CAX-6) represented by the following formula.

Herein, the following peaks were observed by 400 MHz-$^1$H-NMR, and it was confirmed that the compound had a chemical structure of the following formula.

$^1$H-NMR: (d-DMSO, internal standard TMS)
δ (ppm) 9.9 (2H, O—H), 11.3 (1H, N—H), 7.0-7.9 (16H, Ph-H), 6.0 (1H, C—H), 1.5 (3H, CH$_3$)

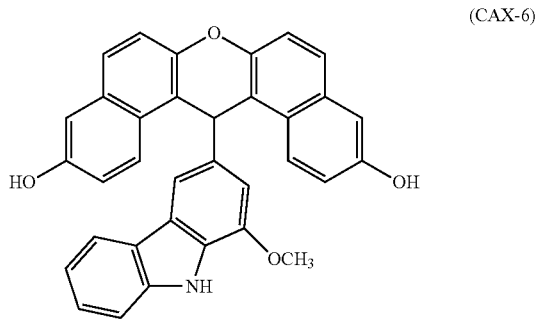 [SMILES: COc1cc(C2c3c(ccc4cc(O)ccc34)Oc3ccc4cc(O)ccc4c32)cc2c1[nH]c1ccccc12]

(CAX-6)

As a result of organic element analysis, the carbon concentration and the oxygen concentration of the resulting compound (CAX-6) were 80.1% and 12.5%, respectively.

The molecular weight of the resulting compound was measured by the above method, and as a result, it was 509.

As a result of thermogravimetric measurement (TG), the 10% thermal weight loss temperature of the resulting compound (CAX-6) was 400° C. or higher. The compound was evaluated to have a high heat resistance and be applicable to high-temperature baking.

As a result of evaluation of the solubility in PGME and PGMEA, the solubility was 10% by weight or more (Evaluation A) and compound (CAX-6) was evaluated to have an excellent solubility. Therefore, compound (CAX-6) was evaluated to have a high storage stability in a solution state and also be sufficiently applicable to an edge bead rinse liquid (mixed liquid of PGME/PGMEA) widely used in a semiconductor microfabrication process.

(Synthesis Example 7) Synthesis of CAX-7

A container having an inner volume of 300 mL, equipped with a stirrer, a condenser and a burette, was prepared. To this container were charged 15.6 g (80 mmol) of 2-hydroxy-9H-carbazole-1-carbaldehyde (synthesized with reference to Francisco, Caria S.; Rodrigues, Ligia R.; Cerqueira, Nuno M. F. S. A.; Oliveira-campos, Ana M. F.; Rodrigues, Ligia M.; Esteves, Ana P.; Bioorganic and Medicinal Chemistry; vol. 21; nb. 17; (2013); p. 5047-5053), 25.6 g (160 mmol) of 2,6-dihydroxynaphthalene (reagent produced by Tokyo Chemical Industry Co., Ltd.) and 100 mL of 1,4-dioxane (reagent produced by Kanto Chemical Co., Inc.), and 3.9 g (21 mmol) of p-toluenesulfonic acid (reagent produced by Kanto Chemical Co., Inc.) was added thereto to prepare a reaction liquid. The reaction liquid was stirred at 90° C. for 8 hours to perform a reaction. Then, a neutralization treatment was performed by a 24% aqueous sodium hydroxide solution (reagent produced by Kanto Chemical Co., Inc.), the reaction liquid was concentrated, 100 g of n-heptane (reagent produced by Kanto Chemical Co., Inc.) was added thereto to precipitate a reaction product, and the resultant was cooled to room temperature followed by filtration for separation. A solid obtained by filtration was dried, and thereafter separated and purified by column chromatography to thereby provide 2.9 g of an objective compound (CAX-7) represented by the following formula.

Herein, the following peaks were observed by 400 MHz-$^1$H-NMR, and it was confirmed that the compound had a chemical structure of the following formula.

$^1$H-NMR: (d-DMSO, internal standard TMS)
δ (ppm) 9.4-9.6 (3H, O—H), 11.2 (1H, N—H), 7.0-7.9 (16H, Ph-H), 6.0 (1H, C—H)

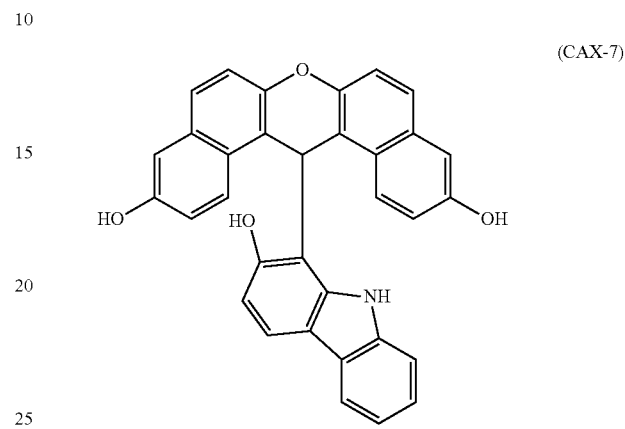

(CAX-7)

As a result of organic element analysis, the carbon concentration and the oxygen concentration of the resulting compound (CAX-7) were 80.0% and 12.9%, respectively.

The molecular weight of the resulting compound was measured by the above method, and as a result, it was 495.

As a result of thermogravimetric measurement (TG), the 10% thermal weight loss temperature of the resulting compound (CAX-7) was 400° C. or higher. The compound was evaluated to have a high heat resistance and be applicable to high-temperature baking.

As a result of evaluation of the solubility in PGME and PGMEA, the solubility was 10% by weight or more (Evaluation A) and compound (CAX-7) was evaluated to have an excellent solubility. Therefore, compound (CAX-7) was evaluated to have a high storage stability in a solution state and also be sufficiently applicable to an edge bead rinse liquid (mixed liquid of PGME/PGMEA) widely used in a semiconductor microfabrication process.

(Synthesis Example 8) Synthesis of Resin (CAR-1)

A four-neck flask having a bottom outlet and an inner volume of 1 L, equipped with a Dimroth condenser, a thermometer and a stirring blade was prepared. To this four-neck flask were charged 35.6 g (70 mmol, produced by Mitsubishi Gas Chemical Company, Inc.) of CAX-1 obtained in Synthesis Example 1, 21.0 g (280 mmol as formaldehyde, produced by Mitsubishi Gas Chemical Company, Inc.) of a 40% by mass aqueous formalin solution and 0.97 mL of 98% by mass sulfuric acid (produced by Kanto Chemical Co., Inc.) under a nitrogen stream, and allowed the reaction to run under ordinary pressure for 7 hours with refluxing at 100° C. Thereafter, 180.0 g of o-xylene (special grade chemical, produced by Wako Pure Chemical Industries, Ltd.) as a dilution solvent was added to the reaction liquid and left to stand, and then an aqueous phase being a bottom phase was removed. Furthermore, the resultant was neutralized and washed with water, and o-xylene was distilled off under reduced pressure, thereby providing 38.2 g of a resin (CAR-1) as a brown solid.

In the resulting resin (CAR-1), Mn was 1885, Mw was 4220 and Mw/Mn was 2.24. In addition, the carbon concentration was 79.8% by mass, and the oxygen concentration was 8.5% by mass.

As a result of thermogravimetric measurement (TG), the 10% thermal weight loss temperature of the resulting resin (CAR-1) was 350° C. or higher and lower than 400° C. Therefore, the resin was evaluated to be applicable to high-temperature baking.

As a result of evaluation of the solubility in PGME and PGMEA, the solubility was 10% by weight or more (Evaluation A) and the resin (CAR-1) was evaluated to have an excellent solubility.

(Synthesis Example 9) Synthesis of Resin (CAR-2)

A four-neck flask having a bottom outlet and an inner volume of 1 L, equipped with a Dimroth condenser, a thermometer and a stirring blade was prepared. To this four-neck flask were charged 35.6 g (70 mmol, produced by Mitsubishi Gas Chemical Company, Inc.) of CAX-1 obtained in Synthesis Example 1, 50.9 g (280 mmol, produced by Mitsubishi Gas Chemical Company, Inc.) of 4-biphenylaldehyde, 100 mL of anisole (produced by Kanto Chemical Co., Inc.) and 10 mL of oxalic acid dihydrate (produced by Kanto Chemical Co., Inc.) under a nitrogen stream, and allowed the reaction to run under ordinary pressure for 7 hours with refluxing at 100° C. Thereafter, 180.0 g of o-xylene (special grade chemical, produced by Wako Pure Chemical Industries, Ltd.) as a dilution solvent was added to the reaction solution and left to stand, and then an aqueous phase being a bottom phase was removed. Furthermore, the resultant was neutralized and washed with water, and the solvent and the unreacted 4-biphenylaldehyde in the organic phase were distilled off under reduced pressure, thereby providing 38.2 g of a resin (CAR-2) as a brown solid.

In the resulting resin (CAR-2), Mn was 2382, Mw was 4610 and Mw/Mn was 1.93. In addition, the carbon concentration was 82.8% by mass, and the oxygen concentration was 7.5% by mass.

As a result of thermogravimetric measurement (TG), the 10% thermal weight loss temperature of the resulting resin (CAR-2) was 350° C. or higher and lower than 400° C. Therefore, the resin was evaluated to be applicable to high-temperature baking.

As a result of evaluation of the solubility in PGME and PGMEA, the solubility was 10% by weight or more (Evaluation A) and the resin (CAR-2) was evaluated to have an excellent solubility.

(Comparative Synthesis Example 1)

A four-neck flask having a bottom outlet and an inner volume of 10 L, equipped with a Dimroth condenser, a thermometer and a stirring blade was prepared. To this four-neck flask were charged 1.09 kg (7 mol, produced by Mitsubishi Gas Chemical Company, Inc.) of 1,5-dimethylnaphthalene, 2.1 kg (28 mol as formaldehyde, produced by Mitsubishi Gas Chemical Company, Inc.) of a 40% by mass aqueous formalin solution and 0.97 mL of 98% by mass sulfuric acid (produced by Kanto Chemical Co., Inc.) under a nitrogen stream, and allowed the reaction to run under ordinary pressure for 7 hours with refluxing at 100° C. Thereafter, ethylbenzene (special grade chemical, produced by Wako Pure Chemical Industries, Ltd.) (1.8 kg) as a dilution solvent was added to the reaction solution and left to stand, and then an aqueous phase being a bottom phase was removed. Furthermore, the resultant was neutralized and washed with water, and ethylbenzene and the unreacted 1,5-dimethylnaphthalene were distilled off under reduced pressure, thereby providing 1.25 kg of a dimethylnaphthalene formaldehyde resin as a light-brown solid.

With respect to the molecular weight of the resulting dimethylnaphthalene formaldehyde, Mn was 562, Mw was 1168 and Mw/Mn was 2.08. In addition, the carbon concentration was 84.2% by mass, and the oxygen concentration was 8.3% by mass.

Subsequently, a four-neck flask having an inner volume of 0.5 L, equipped with a Dimroth condenser, a thermometer and a stirring blade, was prepared. To this four-neck flask were charged 100 g (0.51 mol) of the dimethylnaphthalene formaldehyde resin obtained as described above and 0.05 g of paratoluenesulfonic acid under a nitrogen stream, heated for 2 hours with the temperature being raised to 190° C., and then stirred. Thereafter, 52.0 g (0.36 mol) of 1-naphthol was further added thereto, and further heated to 220° C. to allow the reaction to run for 2 hours. After being diluted with a solvent, the resultant was neutralized and washed with water, and the solvent was removed under reduced pressure to thereby provide 126.1 g of a modified resin (CR-1) as a blackish brown solid.

With respect to the resulting resin (CR-1), Mn was 885, Mw was 2220 and Mw/Mn was 4.17. In addition, the carbon concentration was 89.1% by mass and the oxygen concentration was 4.5% by mass.

As a result of thermogravimetric measurement (TG), the 10% thermal weight loss temperature of the resulting resin (CR-1) was less than 350° C. Therefore, the resin was evaluated to have difficulty in application to high-temperature baking where high etching resistance and heat resistance were required.

As a result of evaluation of the solubility in PGME and PGMEA, the solubility was 10% by weight or more (Evaluation A) and the resin (CR-1) was evaluated to have an excellent solubility.

(Examples 1 to 9 and Comparative Example 1)

Each composition for forming an underlayer film for lithography was prepared so that each composition shown in Table 1 was achieved. That is, the following materials were used.

Acid generating agent: di-tert-butyldiphenyliodonium nonafluoromethanesulfonate (DTDPI) produced by Midori Kagaku Co., Ltd.

Crosslinking agent: Nikalac MX270 (Nikalac) produced by Sanwa Chemical Co., Ltd.

Organic solvent: propylene glycol monomethyl ether acetate (PGMEA)

Novolac: PSM4357 produced by Gun Ei Chemical Industry Co., Ltd.

Then, each composition for forming an underlayer film was spin-coated on a silicon substrate, thereafter baked at 240° C. for 60 seconds and further at 400° C. for 120 seconds to prepare each underlayer film having a film thickness of 200 nm.

An etching test was performed under conditions shown below to evaluate etching resistance. The evaluation results are shown in Table 1.

[Etching Test]

Etching apparatus: RIE-10NR manufactured by Samco Inc.

Output: 50 W
Pressure: 20 Pa
Time: 2 min
Etching Gas
Ar gas flow rate:$CF_4$ gas flow rate:$O_2$ gas flow rate=50:5:5 (sccm)

[Evaluation of Etching Resistance]

The evaluation of etching resistance was performed according to the following procedure.

First, an underlayer film of novolac was prepared under the same conditions as those in Example 1 except that novolac (PSM4357 produced by Gunei Chemical Industry Co., Ltd.) was used instead of the compound (CAX-1) used in Example 1. Then, the etching test was performed with respect to the underlayer film of novolac as a subject, and the etching rate in that time was measured.

Then, the etching resistances were evaluated according to the following criteria based on the etching rate of the underlayer film of novolac.

<Evaluation Criteria>

A; etching rate of less than −10% compared with the underlayer film of novolac

B; etching rate of −10% to +5% compared with underlayer film of novolac

C; etching rate of more than +5% compared with the underlayer film of novolac

TABLE 1

| | Material for forming underlayer film (parts by mass) | Organic solvent (parts by mass) | Acid generating agent (parts by mass) | Cross-linking agent (parts by mass) | Evaluation of etching resistance |
|---|---|---|---|---|---|
| Example 1 | CAX-1 (10) | PGMEA (90) | DTDPI (0.5) | Nikalac (0.5) | A |
| Example 2 | CAX-2 (10) | PGMEA (90) | DTDPI (0.5) | Nikalac (0.5) | A |
| Example 3 | CAX-3 (10) | PGMEA (90) | DTDPI (0.5) | Nikalac (0.5) | A |
| Example 4 | CAX-4 (10) | PGMEA (90) | DTDPI (0.5) | Nikalac (0.5) | B |
| Example 5 | CAX-5 (10) | PGMEA (90) | DTDPI (0.5) | Nikalac (0.5) | A |
| Example 6 | CAX-6 (10) | PGMEA (90) | DTDPI (0.5) | Nikalac (0.5) | A |
| Example 7 | CAX-7 (10) | PGMEA (90) | DTDPI (0.5) | Nikalac (0.5) | A |
| Example 8 | CAR-1 (10) | PGMEA (90) | DTDPI (0.5) | Nikalac (0.5) | B |
| Example 9 | CAR-2 (10) | PGMEA (90) | DTDPI (0.5) | Nikalac (0.5) | B |
| Comparative Example 1 | CR-1 (10) | PGMEA (90) | DTDPI (0.5) | Nikalac (0.5) | C |

Example 10

Then, the composition for forming an underlayer film for lithography in Example 1 was coated on a $SiO_2$ substrate having a film thickness of 300 nm, and baked at 240° C. for 60 seconds and further at 400° C. for 120 seconds to thereby form an underlayer film having a film thickness of 70 nm. A resist solution for ArF was coated on the underlayer film, and baked at 130° C. for 60 seconds to thereby form a photoresist layer having a film thickness of 140 nm.

Herein, as the resist solution for ArF, one prepared by blending 5 parts by mass of the compound of the following formula (11), 1 part by mass of triphenylsulfonium nonafluoromethanesulfonate, 2 parts by mass of tributylamine, and 92 parts by mass of PGMEA was used.

A compound of formula (11) was prepared as follows. That is, 4.15 g of 2-methyl-2-methacryloyloxyadamantane, 3.00 g of methacryloyloxy-γ-butyrolactone, 2.08 g of 3-hydroxy-1-adamantyl methacrylate and 0.38 g of azobisisobutyronitrile were dissolved in 80 mL of tetrahydrofuran to provide a reaction solution. This reaction solution was subjected to polymerization under a nitrogen atmosphere for 22 hours with the reaction temperature being kept at 63° C., and thereafter the reaction solution was dropped in 400 mL of n-hexane. A product resin thus obtained was solidified and purified, and a white powder produced was taken by filtration and dried under reduced pressure at 40° C. overnight to provide a compound represented by the following formula.

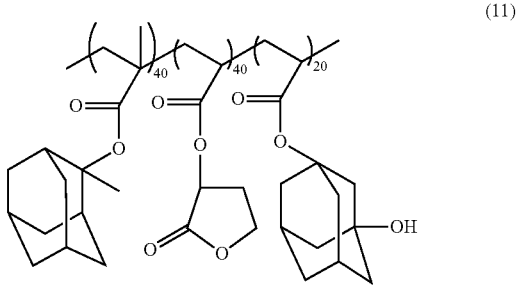

(11)

In the formula (11), the numerals 40, 40, and 20 indicate the proportions of the respective constituent units, and do not mean a block copolymer.

Then, the photoresist layer was exposed by using an electron beam lithography apparatus (ELS-7500, produced by Elionix, Inc., 50 keV), baked at 115° C. for 90 seconds (PEB), and developed with a 2.38% by mass aqueous tetramethylammonium hydroxide (TMAH) solution for 60 seconds, thereby providing a positive-type resist pattern.

(Comparative Example 2)

Except that no underlayer film was formed, the same manner as in Example 7 was performed to form a photoresist layer directly on a $SiO_2$ substrate to provide a positive-type resist pattern.

[Evaluation]

The shapes of the resist patterns of 40 nm L/S (1:1) and 80 nm L/S (1:1) provided in each of Example 10 and Comparative Example 2 were observed by using an electron microscope (S-4800) manufactured by Hitachi Ltd. A case where the shape of the resist pattern after development had no pattern collapse and had good rectangularity was evaluated to be good and a case the shape had pattern collapse and did not have good rectangularity was evaluated to be poor. In the observation results, the minimum line width where there was no pattern collapse and rectangularity was good was defined as the resolution and used as an evaluation index. Furthermore, the minimum amount of electron beam energy, where a good pattern shape could be drawn, was defined as the sensitivity and used as an evaluation index. The results are shown in Table 2.

TABLE 2

| | Material for forming underlayer film | Resolution (nmL/S) | Sensitivity (μC/cm$^2$) | Resist pattern formation after development |
|---|---|---|---|---|
| Example 10 | Material described in Example 1 | 40 | 20 | Good |
| Comparative Example 2 | Not used | 90 | 38 | Poor |

As can be seen from Table 2, it was confirmed that the underlayer film obtained in Example 10 was significantly excellent in resolution and sensitivity as compared with that in Comparative Example 2. It was also confirmed that the resist pattern shape after development had no pattern collapse and had good rectangularity. Furthermore, it was shown from the difference in the resist pattern shape after development that the material for forming an underlayer film for lithography in Example 1 had good adhesiveness with a resist material.

(Example 11) Purification of CAX-1

To a four-neck flask (bottom outlet type) having a volume of 1000 mL was charged 300 g of a solution (5% by mass) in which CAX-1 obtained in Example 1 was dissolved in PGMEA, and heated to 80° C. with stirring. Then, 74 g of an aqueous oxalic acid solution (pH: 1.3) was added thereto, stirred for 5 minutes and thereafter left to stand for 30 minutes. The resultant was thus separated to an oil phase and an aqueous phase, and therefore the aqueous phase was removed. Such an operation was repeated once, and thereafter the resulting oil phase was charged with 74 g of ultrapure water, stirred for 5 minutes and thereafter left to stand for 30 minutes to remove the aqueous phase. Such an operation was repeated three times, and thereafter the flask was subjected to pressure reduction to 200 hPa or less while being heated to 80° C., to thereby allow the remaining water content and PGMEA to be distilled off by concentration. Thereafter, dilution with PGMEA (EL grade, reagent produced by Kanto Chemical Co., Inc.) was made to adjust the concentration to 10% by mass, thereby providing a solution of CAX-1 having a reduced metal content, in PGMEA.

The contents of various metals were measured by ICP-MS with respect to the 10% by mass CAX-1 solution in PGMEA before treatment, and the solution obtained in Example 11. The measurement results are shown in Table 3.

TABLE 3

| | Metal content (ppb) | | | | | |
|---|---|---|---|---|---|---|
| | Na | Mg | K | Fe | Cr | Sn |
| Before treatment CAX-1 | >99 | 23.2 | >99 | >99 | 10.7 | 13.6 |
| Example 11 | 0.7 | 0.9 | 0.6 | 1.2 | 1.3 | 1.4 |

The compound and the resin of the present invention have a relatively high heat resistance and also a relatively high solvent solubility, and which can be applied to a wet process. Therefore, a material for forming an underlayer film for lithography and an underlayer film, using the compound or the resin of the present invention, can be widely and effectively utilized in various applications in which these properties are required. Therefore, the present invention can be widely and effectively utilized for, for example, a coating agent for a semiconductor, a resist resin for a semiconductor, and a resin for forming an underlayer film. In particular, the present invention can be particularly effectively utilized in the field of an underlayer film for lithography and an underlayer film for a multilayer resist.

The invention claimed is:

1. A material for forming an underlayer film for lithography comprising a compound represented by the following formula (1-4):

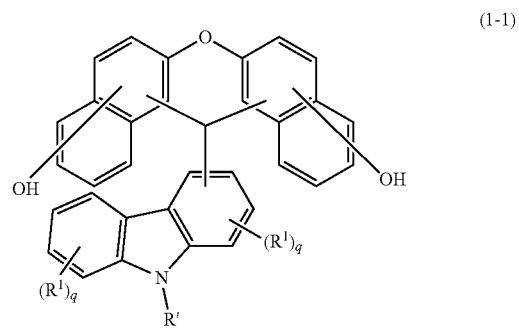

(1-1)

wherein each $R^1$ is independently selected from the group consisting of a hydrogen atom, a halogen group, a nitro group, an amino group, a hydroxyl group, an alkyl group having 1 to 30 carbon atoms, an alkenyl group having 2 to 30 carbon atoms, an aryl group having 6 to 40 carbon atoms and combinations thereof, in which the alkyl group, the alkenyl group and the aryl group may have an ether bond, a ketone bond or an ester bond, and each q is independently an integer of 0 to 4.

2. The material for forming an underlayer film for lithography according to claim 1, wherein the compound represented by the formula (1-4) is a compound represented by the following formula (CAX-1):

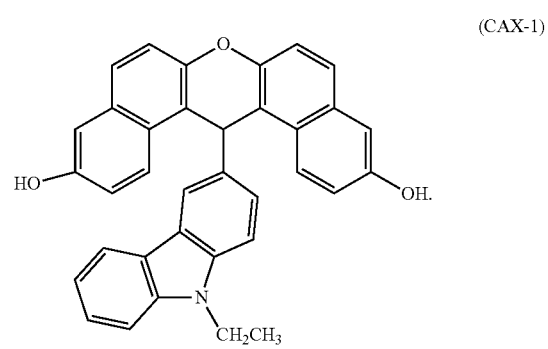 [SMILES: CCn1c2ccccc2c2cc(C3c4c(ccc5cc(O)ccc45)Oc4ccc5cc(O)ccc5c43)ccc21]

(CAX-1)

3. A composition for forming an underlayer film for lithography, comprising the material for forming an underlayer film for lithography according to claim 1, and a solvent.

4. The composition for forming the underlayer film for lithography according to claim 3, further comprising an acid generating agent.

5. The composition for forming the underlayer film for lithography according to claim 3, further comprising a crosslinking agent.

6. An underlayer film for lithography, formed from the composition for forming the underlayer film for lithography according to claim 3.

7. A resist pattern forming method comprising
step (A-1) of forming an underlayer film on a substrate by using the composition for forming the underlayer film for lithography according to claim 3,
step (A-2) of forming at least one photoresist layer on the underlayer film, and
step (A-3) of, after step (A-2), irradiating a predetermined region of the photoresist layer with radiation, followed by developing.

8. A circuit pattern forming method comprising
step (B-1) of forming an underlayer film on a substrate by using the composition for forming the underlayer film for lithography according to claim 3,
step (B-2) of forming an intermediate layer film on the underlayer film by using a silicon atom-containing resist intermediate layer film material,
step (B-3) of forming at least one photoresist layer on the intermediate layer film,
step (B-4) of, after step (B-3), irradiating a predetermined region of the photoresist layer with radiation, followed by developing to form a resist pattern, and
step (B-5) of, after step (B-4), etching the intermediate layer film with the resist pattern as a mask, etching the underlayer film with the obtained intermediate layer film pattern as an etching mask and etching the substrate with the obtained underlayer film pattern as an etching mask, to form a pattern on the substrate.

9. A method for purifying the compound used in the material for forming an underlayer film for lithography according to claim 1, the method comprising
a step of bringing a solution comprising an organic solvent optionally immiscible with water and the compound or the resin into contact with an acidic aqueous solution for extraction.

10. The method according to claim 9, wherein the acidic aqueous solution is an aqueous solution of at least one mineral acid selected from the group consisting of hydrochloric acid, sulfuric acid, nitric acid and phosphoric acid, or an aqueous solution of at least one organic acid selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid and trifluoroacetic acid.

11. The method according to claim 9, wherein the organic solvent optionally immiscible with water is toluene, 2-heptanone, cyclohexanone, cyclopentanone, methyl isobutyl ketone, propylene glycol monomethyl ether acetate, 1,2-diethoxyketone, butyl acetate or ethyl acetate.

12. A resin having a structure represented by the following formula (1-4):

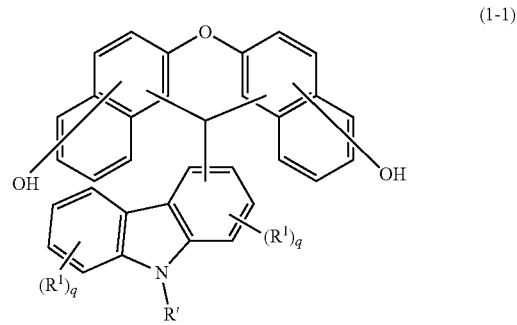

(1-1)

wherein each $R^1$ is independently selected from the group consisting of a hydrogen atom, a halogen group, a nitro group, an amino group, a hydroxyl group, an alkyl group having 1 to 30 carbon atoms, an alkenyl group having 2 to 30 carbon atoms, an aryl group having 6 to 40 carbon atoms and combinations thereof, in which the alkyl group, the alkenyl group and the aryl group may have an ether bond, a ketone bond or an ester bond, and each q is independently an integer of 0 to 4.

* * * * *

UNITED STATES PATENT AND TRADEMARK OFFICE
CERTIFICATE OF CORRECTION

PATENT NO. : 10,577,323 B2
APPLICATION NO. : 15/557747
DATED : March 3, 2020
INVENTOR(S) : Kana Okada et al.

It is certified that error appears in the above-identified patent and that said Letters Patent is hereby corrected as shown below:

In the Claims

Column 56, Lines (1-15):

In Claim 1, please delete " 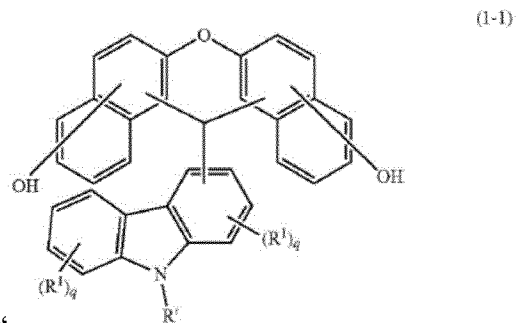 " and insert

-- 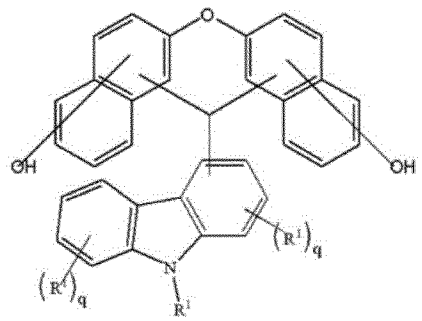 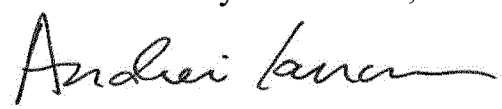 --, therefor.

Signed and Sealed this
Thirteenth Day of October, 2020

Andrei Iancu
*Director of the United States Patent and Trademark Office*

CERTIFICATE OF CORRECTION (continued)
U.S. Pat. No. 10,577,323 B2

Column 58, Lines (8-23):

In Claim 12, please delete " 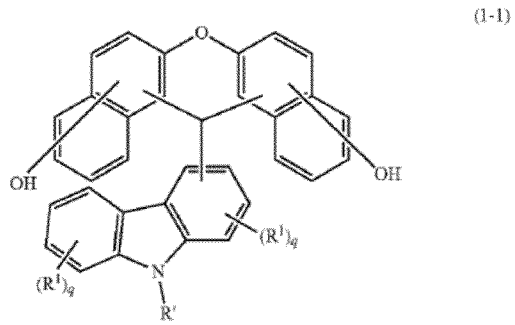 " and insert

-- 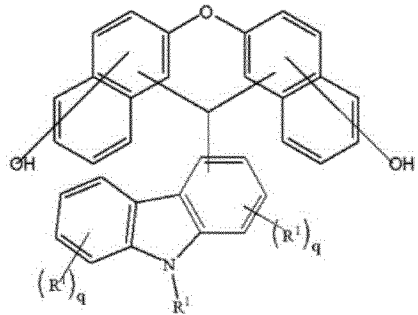 --, therefor.